United States Patent [19]
Lohray et al.

[11] Patent Number: 6,011,036
[45] Date of Patent: Jan. 4, 2000

[54] HETEROCYCLIC COMPOUNDS HAVING ANTIDIABETIC HYPOLIPIDEMIC ANTIHYPERTENSIVE PROPERTIES PROCESS FOR THEIR PREPARATION AND PHARMACEUTICAL COMPOSITIONS CONTAINING THEM

[75] Inventors: Vidya Bhushan Lohray; Braj Bhushan Lohray; Ranga Madhavan Gurram; Rajagopalan Ramanujam; Ranjan Chakrabarti, all of Hyderabad, India

[73] Assignees: Dr. Reddy's Research Foundation, Hyderabad, India; Reddy-Cheminor, Inc., Ridgewood, N.J.

[21] Appl. No.: 08/982,962

[22] Filed: Dec. 2, 1997

[30] Foreign Application Priority Data

Apr. 15, 1997 [IN] India ................ 771/MAS/97

[51] Int. Cl.$^7$ .............. A61K 31/50; A61K 31/535; C07D 237/30; C07D 265/02
[52] U.S. Cl. .............. 514/248; 544/63; 544/116; 544/237; 514/230.5; 514/232.5; 514/233.8
[58] Field of Search .................. 544/237, 116; 514/248, 233.8, 232.5

[56] References Cited

U.S. PATENT DOCUMENTS

| | | | |
|---|---|---|---|
| 4,873,255 | 10/1989 | Yoshioka | 514/369 |
| 5,002,953 | 3/1991 | Hindley | 514/275 |
| 5,037,842 | 8/1991 | Goldstein | 514/375 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,521,201 | 5/1996 | Hindley | 514/342 |

FOREIGN PATENT DOCUMENTS

| | | |
|---|---|---|
| 0139421 | 5/1985 | European Pat. Off. |
| 0306228 | 3/1989 | European Pat. Off. |
| 0356214 | 2/1990 | European Pat. Off. |
| 0419035 | 3/1991 | European Pat. Off. |
| 0604983 | 7/1994 | European Pat. Off. |
| 0612743 | 8/1994 | European Pat. Off. |
| 0745600 | 12/1996 | European Pat. Off. |
| 0783888 | 7/1997 | European Pat. Off. |
| 0787727 | 8/1997 | European Pat. Off. |
| 0903343 | 9/1998 | European Pat. Off. |
| 0912575 | 1/1997 | Japan . |
| 9112003 | 8/1991 | WIPO . |
| 9207838 | 5/1992 | WIPO . |
| 9207839 | 5/1992 | WIPO . |
| 9425026 | 11/1994 | WIPO . |
| 9507697 | 3/1995 | WIPO . |
| 9521608 | 8/1995 | WIPO . |
| 9526347 | 8/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |

OTHER PUBLICATIONS

Bernard et al., "A New and Efficient Synthesis of Phthalazin–1(2H)–ones," Synthesis, vol. 3, pp. 317–320, Mar. 1998.

Messier, C. et al., Behavioral Brain Research, 75 (1966) 1–11.

Sohda, T. et al., Chem Pharm Bull. 30, 10 (1982), 3580–3600.

Clark, et al. J. Med. Chem 34 (1991) 319–325.

Dow, R. L. et al., J. Med. Chem 34 (1991) 1538–1544.

Hulin, et al., J. Med. Chem 35 (1992) 1853–1864.

Sohda, T. et al., J. Med. Chem 35 (1992) 2617–2626.

Goldsein, et al., J. Med. Chem. 36 (1993) 2238–2240.

Cantello, et al., J. Med. Chem 37 (1994) 3977–3985.

English Translation of JP–A–0912575.

M. Modan, et al., J. Clin. Invest. (1985) vol. 75, pp. 809–817.

O. G. Kolterman, et al., J. Clin. Invest. (1981) vol. 68, pp. 957–969.

E. Ferrannini, et al., The New England Journal of Medicine (1987) vol. 317, pp. 350–357.

D.C. Shen, et al., J. Clin. Endocrinol. Metab. (1988) vol. 66, pp. 580–583.

Goodman & Gilman's The Pharmacological Basis of Therapeutics, Ninth Edition, pp. 1496–1497.

Clifford Bailey, "Potential New Treatments for Type 2 Diabetes", Chemistry & Industry, Jan. 19, 1998, pp. 53–57.

t. Antonucci et al., "Imparied Glucose Tolerance is Normalized by Treatment with the Thiazolidinedione Troglitazone" Diabetes Care, vol. 20, No. 2, Feb. 1997, pp. 188–193.

Cantello, Barrie C. C., et al. "Omega (Heterocyclylamino)alkoxy[benzyl]–2,4–thiazolidinediones as Potent Antihyperglycemic Agents." Journal of Medical Chemistry, vol. 37, No. 23 (1994) pp. 3977–3985.

*Primary Examiner*—Mukund J. Shah
*Assistant Examiner*—Ann M. Kessinger
*Attorney, Agent, or Firm*—Ladas & Parry

[57] ABSTRACT

The present invention relates to novel antidiabetic compounds, their tautomeric forms, their analogues, their derivatives, their stereoisomers, their polymorphs, their pharmaceutically acceptable salts, their pharmaceutically acceptable solvates and pharmaceutically acceptable compositions containing them. This invention particularly relates to novel azolidinedione compounds of the general formula (I), and their analogues, their derivatives, their tautomeric forms, their stereoisomers, their polymorphs, their pharmaceutically acceptable salts, pharmaceutically acceptable solvates and pharmaceutical compositions containing them.

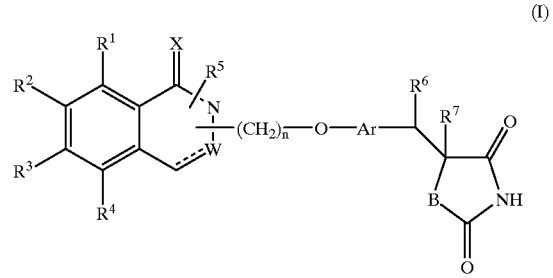

19 Claims, No Drawings

HETEROCYCLIC COMPOUNDS HAVING ANTIDIABETIC HYPOLIPIDEMIC ANTIHYPERTENSIVE PROPERTIES PROCESS FOR THEIR PREPARATION AND PHARMACEUTICAL COMPOSITIONS CONTAINING THEM

FIELD OF THE INVENTION

The present invention relates to novel antidiabetic compounds, their tautomeric forms, their analogues, their derivatives, their stereoisomers, their polymorphs, their pharmaceutically acceptable salts, their pharmaceutically acceptable solvates and pharmaceutically acceptable compositions containing them. This invention particularly relates to novel azolidinedione compounds of the general formula (I), and their analogues, their derivatives, their tautomeric forms, their stereoisomers, their polymorphs, their pharmaceutically acceptable salts, pharmaceutically acceptable solvates and pharmaceutical compositions containing them.

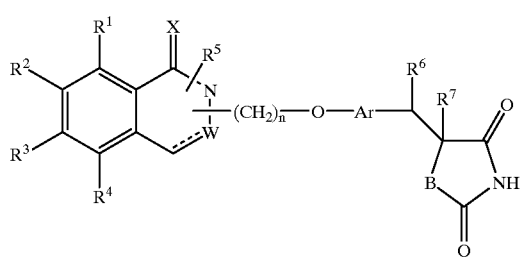

The present invention also relates to a process for the preparation of the above said novel azolidinedione compounds, their analogues, their derivatives, their tautomeric forms, their stereoisomers, their polymorphs, their pharmaceutically acceptable salts, pharmaceutically acceptable solvates, and pharmaceutical compositions containing them.

This invention also relates to novel intermediates, processes for preparing the intermediates and processes for using intermediates.

The azolidinediones of the general formula (I) defined above of the present invention are useful for the treatment and/or prophylaxis of hyperlipidemia, hypercholesterolemia, hyperglycemia, osteoporosis, obesity, glucose intolerance, insulin resistance and also diseases or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The azolidinediones of the formula (I) are useful for the treatment of insulin resistance associated with obesity and psoriasis. The azolidinediones of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (Patent Application No. WO 95/07697), psoriasis (Patent Application No. WO 95/35108), dementia (Behavioral Brain Research (1996) 75: 1–11) etc. may also have insulin resistance as a central pathogenic feature. Recently, it has also been reported that insulin sensitizers improve the bone mineral density and thus may be useful for the treatment of osteoporosis (EP-783888).

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref. Chem. Pharm. Bull. 1982, 30, 3580–3600). In the formula (II), V represents substituted or unsubstituted divalent aromatic group B represents a sulfur atom or an oxygen atom and U represents various groups which have been reported in various patent documents.

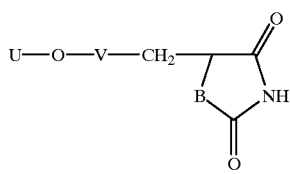

By way of examples, U may represent the following groups:

(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

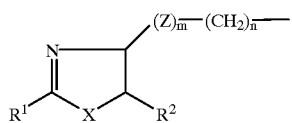
(IIa)

An example of these compounds is shown in formula (IIb)

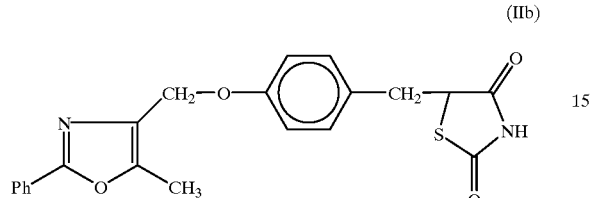
(IIb)

(ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$–$R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

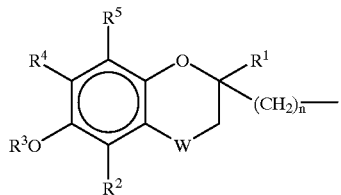
(IIc)

An example of these compounds is shown in (IId)

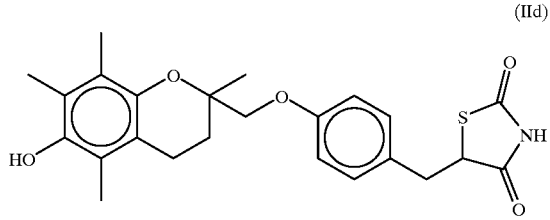
(IId)

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

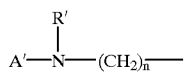
(IIe)

An example of this compound is shown in formula (IIf)

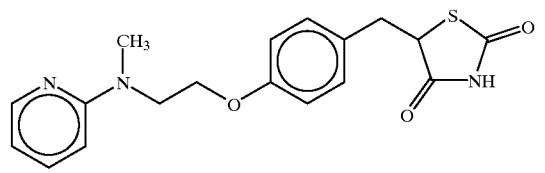
(IIf)

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

(IIg)

An example of this compound is shown in formula (IIh)

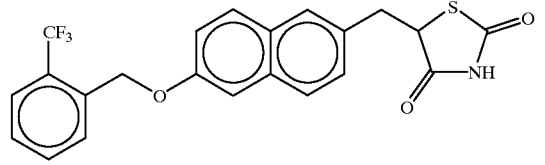
(IIh)

v) a group of formula (IIi), where R is ($C_1$–$C_6$) alkyl groups, cycloalkyl group, furyl, thienyl, substituted or unsubstituted phenyl group, X is hydrogen, methyl, methoxy, chloro or fluoro. These compounds have been disclosed in the U.S. Pat. No. 5,037,842.

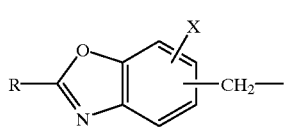
(IIi)

An example of these compounds is shown in formula (IIj).

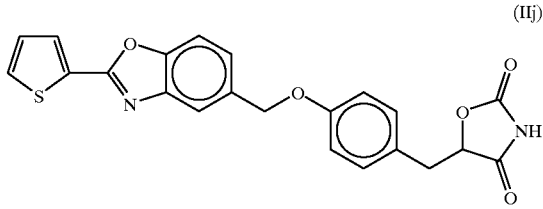

(IIj)

(vi) a group of formula (IIk) wherein A¹ represents a substituted or unsubstituted aromatic heterocyclyl group; R¹ represents a hydrogen atom, an alkyl group, an acyl group, an aralkyl group, wherein the aryl moiety may be substituted or unsubstituted or a substituted or unsubstituted aryl group, n represents an integer in the range of from 2 to 6. These compounds have been disclosed in the patent application No. WO 92/02520.

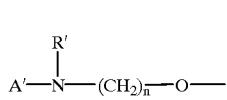

(IIk)

An example of these compounds is shown in formula (II l).

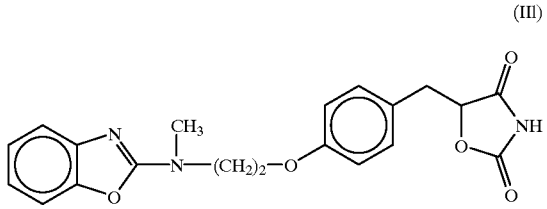

(III)

Some of the above referenced hitherto known antidiabetic compounds seem to possess bone marrow depression, liver and cardiac toxicities and modest potency and consequently, their regular use for the treatment and control of diabetes is becoming limited and restricted.

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel azolidinedione compounds having the general formula (I) as defined above.

The main objective of the present invention is therefore, to provide novel azolidinediones, their derivatives, their analogues, their tautomeric forms, their stereoisomers, their polymorphs, their pharmaceutically acceptable salts, their pharmaceutically acceptable solvates and pharmaceutical compositions containing them, or mixtures thereof.

Another objective of the present invention is to provide novel azolidinediones, their derivatives, their analogues, their tautomeric forms, their stereoisomers, their polymorphs, their pharmaceutically acceptable salts, their pharmaceutically acceptable solvates and pharmaceutical compositions containing them or mixtures thereof having enhanced activities, no toxic effect or reduced toxic effect.

Yet another objective of the present invention is to produce a process for the preparation of novel azolidinediones of the formula (I) as defined above, their derivatives, their analogues, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their derivatives, their analogues, their tautomers, their stereoisomers, their polymorphs, their pharmaceutically acceptable salts, solvates or mixtures thereof in combination with suitable carriers, solvents, excipients, diluents and other media normally employed in preparing such compositions.

Yet another objective of the present invention is to provide a novel intermediate of the formula (III)

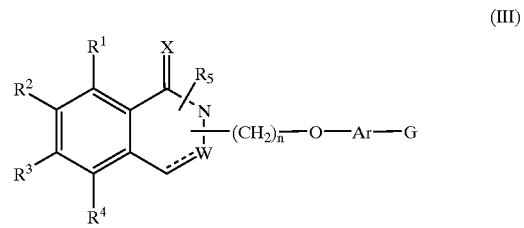

(III)

where G represents —CHO, —NO₂, —NH₂ or —CH₂CH(J)—COOR, where J represents halogen atom such as chlorine, bromine or iodine and R represents H or lower alkyl group such as a ($C_1$–$C_6$) alkyl, preferably a ($C_1$–$C_3$) alkyl group such as methyl, ethyl, or propyl; and $R^1$, $R^2$, $R^3$, $R^4$, $R^5$, X, W, n and Ar are defined as in formula (I) and a process for the preparation thereof.

DETAILED DESCRIPTION OF THE INVENTION

Azolidinediones of the present invention have the general formula (I)

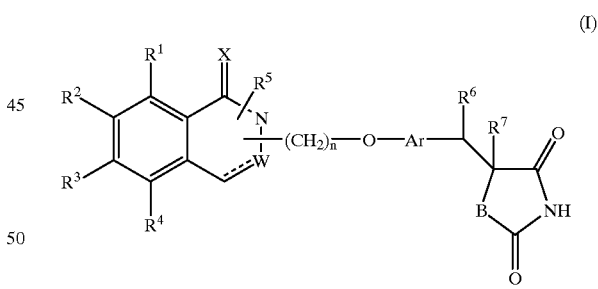

(I)

In the above formula (I), X represents O or S; the groups $R^1$, $R^2$, $R^3$, $R^4$ may be same or different and represent hydrogen, halogen, hydroxy, cyano, nitro; optionally substituted groups selected from alkyl, cycloalkyl, alkoxy, cycloalkyloxy, aryl, aralkyl, heteroaryl, heteroaralkyl, heterocyclyl, aryloxy, alkoxycarbonyl, aryloxycarbonyl, aralkoxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; "----" represents a bond or no bond; W represents oxygen atom or nitrogen atom, with the provision that when W represents nitrogen atom, "----" represents a bond and when W represents a oxygen atom "----" represents no bond; when $R^5$ is present on a carbon atom, it represents hydrogen, hydroxy, halogen, nitro, cyano, optionally substituted groups selected from amino, alkyl, cycloalkoxy, cycloalkyl, acylamino, aryl, aralkyl, heterocyclyl, heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its derivatives, sulfonic acid and its derivatives; when $R^5$ is present on a nitrogen atom, it represents hydrogen, optionally substituted groups selected from alkyl, cycloalkyl, aryl, aralkyl, heterocyclyl, heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, carboxylic acid derivatives, or sulfonic acid derivatives; n is an integer ranging from 1–4; Ar represents an optionally substituted divalent aromatic or heterocyclic group; $R^6$ and $R^7$ may be same or different and individually represent hydrogen atom, hydroxy, halogen or lower alkyl group or together form a bond; B represents an oxygen atom or a sulfur atom.

Suitable groups represented by $R^1$, $R^2$, $R^3$, $R^4$ may be selected from hydrogen, halogen atom such as fluorine, chlorine, bromine, or iodine; hydroxy, cyano, nitro; substituted or unsubstituted $(C_{1-2})$alkyl group, especially, linear or branched $(C_1-C_6)$alkyl group, such as methyl, ethyl, n-propyl, isopropyl, n-butyl, iso-butyl, t-butyl, n-pentyl, isopentyl, hexyl and the like; cycloalkyl group such as cyclopropyl, cyclobutyl, cyclopentyl, cyclohexyl and the like, the cycloalkyl group may be substituted; cycloalkyloxy group such as cyclopropyloxy, cyclobutyloxy, cyclopentyloxy, cyclohexyloxy and the like, the cycloalkoxy group may be substituted; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heteroaralkyl wherein the heteroaryl moiety is as defined earlier and is attached to $(C_1–C_3)$ alkylene moiety such as furanmethyl, pyridinemethyl, oxazolemethyl, oxazolethyl and the like; heterocyclyl groups such as aziridinyl, pyrrolidinyl, morpholinyl, piperidinyl, piperazinyl and the like, the heterocyclyl group may be substituted; aryloxy such as phenoxy, naphthyloxy, the aryloxy group may be substituted; alkoxycarbonyl such as methoxycarbonyl or ethoxycarbonyl, the alkoxycarbonyl group may be substituted; aryloxyvcarbonyl group such as phenoxycarbonyl or naphthyloxy carbonyl, the aryloxycarbonyl group may be substituted; aralkoxycarbonyl wherein the aryl moiety is phenyl or naphthyl; aralkoxycarbonyl group such as benzyloxycarbonyl, phenethyloxycarbonyl, napththylmethyloxycarbonyl and the like, the aralkoxycarbonyl group may be substituted; linear or branched $(C_1–C_6)$alkylamino, the alkylamino group may be substituted; arylamino group such as $HNC_6H_5$, $NCH_3C_6H_5$, $—NHC_6H_4—CH_3$, $NHC_6H_4$-halo and the like, the arylamino group may be substituted; amino group; amino$(C_1–C_6)$alkyl group, the aminoalkyl group may be substituted; hydroxy$(C_1–C_6)$alkyl group, the hydroxyalkyl group may be substituted; $(C_1–C_6)$ alkoxy group, the alkoxy group may be substituted; thio $(C_1–C_6)$alkyl group, thioalkyl group may be substituted; $(C_1–C_6)$alkylthio group, the alkylthio group may be substituted; acyl group such as acetyl, propionyl or benzoyl, the acyl group may be substituted; acylamino group such as $NHCOCH_3$, $NHCOC_2H_5$, $NHCOC_3H_7$, $NHCOC_6H_5$, the acylamino group may be substituted, aryloxycarbonylamino group such as $NHCOOC_6H_5$, $—NCH_3COOC_6H_5$, $—NC_2H_5COOC_6H_5$, $—NHCOOC_6H_4CH_3$, $—NHCOOC_6H_4OCH_3$ and the like, the aryloxycarbonylamino may be substituted, aralkoxycarbonylamino group such as $NHCOOCH_2C_6H_5$, $—NHCOOCH_2CH_2C_6H_5$, $—NCH_3COOCH_2C_6H_5$, $—NC_2H_5COOCH_2C_6H_5$, $—NHCOOCH_2C_6H_4CH_3$, $—NHCOOCH_2C_6H_4OCH_3$ and the like, aralkoxycarbonylamino may be substituted; alkoxycarbonyl amino group such as, $NHCOOC_2H_5$, $NHCOOCH_3$ and the like, alkoxycarbonyl group may be substituted; carboxylic acid or its derivatives such as amides, like $CONH_2$, $CONHMe$, $CONMe_2$, $CONHEt$, $CONEt_2$, $CON-HPh$ and the like, the carboxylic acid derivatives may be substituted; acyloxy group such as MeCOO, EtCOO, PhCOO and the like, the acyloxy which may optionally be substituted; sulfonic acid or its derivatives such as $SO_2NH_2$, $SO_2NHMe$, $SO_2NMe_2$, $SO_2NHCF_3$ and the like, the sulfonic acid derivatives may be substituted.

When the groups represented by $R^1$, $R^2$, $R^3$, $R^4$ are substituted, the substituents may be selected from halogen, hydroxy, cyano or nitro or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl, alkoxycarbonylamino, aryloxycarbonylamino, aralkoxycarbonylamino, carboxylic acid or its derivatives, or sulfonic acid or its derivatives. The substituents are as defined above.

It is preferred that $R^1$–$R^4$ represent hydrogen, halogen atom such as fluorine, chlorine, bromine; alkyl group such as methyl, ethyl, isopropyl, n-propyl, n-butyl and the like which may be halogenated; optionally halogenated groups selected from cycloalkyl group such as cyclopropyl; aryl group such as phenyl; aralkyl group such as benzyl; $(C_1–C_3)$ alkoxy, aryloxy group such as benzyloxy, hydroxy group, acyl or acyloxy groups. Acyl and acyloxy groups are as defined above.

When $R^5$ is attached to carbon atom, suitable groups represented by $R^5$ are selected from hydrogen, halogen atom such as fluorine, chlorine, bromine, or iodine; hydroxy, nitro, cyano; substituted or unsubstituted $(C_1–C_{12})$alkyl group, especially, linear or branched $(C_1–C_6)$alkyl group, such as methyl, ethyl, n-propyl, isopropyl, n-butyl, iso-butyl, t-butyl and the like; cycloalkyl group such as cyclopropyl, cyclobutyl, cyclopentyl, cyclohexyl and the like, the cycloalkyl group may be substituted; cycloalkyloxy group such as cyclopropyloxy, cyclobutyloxy, cyclopentyloxy, cyclohexyloxy and the like, the cycloalkoxy group may be substituted; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl and the like, the heterocyclyl group may be substituted; aryloxy such as phenoxy, naphthyloxy, the aryloxy group may be substituted; alkoxycarbonyl such as methoxycarbonyl or ethoxycarbonyl; aryloxycarbonyl group such as optionally substituted phenoxycarbonyl; aralkoxycarbonyl wherein the aralkyl moiety is as defined earlier; arylamino group such as $HNC_6H_5$, $—NCH_3C_6H_5$, —NHC$_6$H$_4$—CH$_3$,—HNC$_6$H$_4$—halo and the like; amino group; amino(C$_1$–C$_6$)alkyl; hydroxy(C$_1$–C$_6$)alkyl; (C$_1$–C$_6$) alkoxy; thio(C$_1$–C$_6$)alkyl; (C$_1$–C$_6$)alkylthio; acyl group such as acetyl, propionyl or benzoyl, the acyl group may be substituted; acylamino groups such as NHCOCH$_3$, NHCOC$_2$H$_5$, NHCOC$_3$H$_7$, NHCOC$_6$H$_5$, aryloxycarbonylamino group such as NHCOOC$_6$H$_5$, —NCH$_3$COOC$_6$H$_5$, —NC$_2$H$_5$COOC$_6$H$_5$, —NHCOOC$_6$H$_4$CH$_3$, —NHCOOC$_6$H$_4$OCH$_3$ and the like; aralkoxycarbonylamino group such as NHCOOCH$_2$C$_6$H$_5$, NHCOOCH$_2$CH$_2$C$_6$H$_5$, NCH$_3$COOCH$_2$C$_6$H$_5$, —NC$_2$H$_5$COOCH$_2$C$_6$H$_5$, —NHCOOCH$_2$C$_6$H$_4$CH$_3$, —NHCOOCH$_2$C$_6$H$_4$OCH$_3$ and the like; alkoxycarbonylamino group such as NHCOOC$_2$H$_5$, NHCOOCH$_3$ and the like; alkylamino group such as methylamino, ethylamino, propylamino and the like; aralkoxy group such as benzyloxy, phenethyloxy and the like; alkoxyalkyl group such as methoxymethyl, methoxyethyl, ethoxymethyl, ethoxyethyl and the like; heteroaralkyl group such as furanmethyl, pyridinemethyl, oxazolemethyl, oxazolethyl and the like; carboxylic acid or its derivatives such as amides, like CONH$_2$, CONHMe, CONMe$_2$, CONHEt, CONEt$_2$, CONHPh and the like, the carboxylic acid derivatives may be substituted; acyloxy group such as OCOMe, OCOEt, OCOPh and the like which may optionally be substituted; sulfonic acid or its derivatives such as SO$_2$NH$_2$, SO$_2$NHMe, SO$_2$NMe$_2$, SO$_2$NHCF$_3$ and the like; the sulfonic acid derivatives may be substituted.

When R$^5$ is attached to nitrogen atom, suitable groups represented by R$^5$ are selected from (C$_1$–C$_{12}$)alkyl group, especially linear or branched (C$_1$–C$_6$)alkyl group, such as methyl, ethyl, n-propyl, isopropyl, n-butyl, iso-butyl, t-butyl groups and the like; cycloalkyl group such as cyclopropyl, cyclobutyl, cyclopentyl, cyclohexyl and the like, the cycloalkyl group may be substituted; aryl group such as phenyl or naphthyl; aralkyl such as benzyl or phenethyl; heteroaryl group such as pyridyl, thienyl, furyl, pyrrolyl, oxazolyl, thiazolyl, oxadiazolyl, tetrazolyl and the like; heterocyclyl groups such as aziridinyl, pyrrolidinyl, morpholinyl, piperidinyl and the like; alkoxycarbonyl such as methoxycarbonyl or ethoxycarbonyl; aryloxycarbonyl group such as phenoxycarbonyl or naphthyloxycarbonyl; amino(C$_1$–C$_6$)alkyl; hydroxy(C$_1$–C$_6$)alkyl; thio(C$_1$–C$_6$) alkyl; or acyl group such as acetyl, propionyl, benzoyl, and the like; carboxylic acid derivatives such as amides, like CONH$_2$, CONHMe, CONMe$_2$, CONHEt, CONEt$_2$, CONHPh and the like, the carboxylic acid derivatives may be substituted; acyloxy group such as OCOMe, OCOEt, OCOPh and the like which may optionally be substituted; sulfonic acid derivatives such as SO$_2$NH$_2$, SO$_2$NHMe, SO$_2$NMe$_2$, SO$_2$NHCF$_3$ and the like; the sulfonic acid derivatives may be substituted; aryloxy such as phenoxy or naphthyloxy and the like; the aryloxy group may be substituted; (C$_1$–C$_6$)alkoxy; aralkoxy group such as benzyloxy, phenethyloxy and the like; alkoxyalkyl group such as methoxymethyl, methoxyethyl, ethoxymethyl, ethoxyethyl and the like; aralkoxycarbonyl wherein the aralkyl moiety is as defined earlier; heteroaralkyl group such as furanmethyl, pyridinemethyl, oxazolemethyl, oxazolethyl and the like.

All the groups that may represent R$^5$ may be substituted or unsubstituted.

When the groups represented by R$^5$ are substituted, the substituents selected are from the same groups as those groups that represent R$^5$ attached to carbon atom and may be selected from halogen, hydroxy, cyano or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl, carboxylic acid or its derivatives, or sulfonic acid or its derivatives.

When the groups represented by R$^5$ are substituted, preferred substituents are selected from halogen such as fluorine, chlorine; hydroxy, acyl, acyloxy, amino, alkyl, aralkyl, aryl, alkoxy, aralkoxy groups.

The substituents are defined as above.

n is an integer ranging from 1–4. It is preferred that n be 1 or 2.

It is preferred that the group represented by Ar be substituted or unsubstituted groups selected from divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl, benzoxazolyl and the like. The substituents on the group represented by Ar may be selected from linear or branched (C$_1$–C$_6$)alkyl, (C$_1$–C$_3$)alkoxy, halogen, acyl, amino, acylamino, thio, or carboxylic or sulfonic acids or their derivatives.

It is more preferred that Ar represents substituted or unsubstituted divalent phenylene, naphthylene, benzofuryl, indolyl, indolinyl, quinolinyl, azaindolyl, azaindolinyl, benzothiazolyl or benzoxazolyl.

It is still more preferred that Ar is represented by divalent phenylene or naphthylene, which may be optionally substituted by methyl, halomethyl, methoxy or halomethoxy groups.

When Ar is substituted the substituents are as defined above.

Suitable R$^6$ includes hydrogen, hydroxy, lower alkyl group such as a (C$_1$–C$_6$) alkyl such as methyl, ethyl, propyl and the like; halogen atom such as fluorine, chlorine, bromine or iodine; or R$^6$ together with R represents a bond.

It is preferred that R$^6$ represents hydrogen or a bond together with R$^7$.

Suitable R$^7$ may be a hydrogen atom, halogen, lower alkyl group such as (C$_1$–C$_6$) alkyl such as methyl, ethyl, propyl and the like; or together with R$^6$ forms a bond.

When R$^6$ or R$^7$ is lower alkyl, the lower alkyl may be substituted by groups such as halogen, methyl or oxo group.

Suitable B group includes a hetero atom selected from O or S.

Suitable ring structure comprising B include 2,4-dioxooxazolidinyl, or 2,4-dioxothiazolidinyl.

It is more preferred that the ring structure comprising B is a 2,4-dioxothiazolidinyl group.

The groups represented by R$^1$–R$^7$ and any substituent on these groups may be defined as disclosed anywhere in the specification.

Pharmaceutically acceptable salts forming part of this invention include salts of the azolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts; alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

5-[4-[2-[4-Methyl-1-oxo-1,2-dihydro-phthalazin-2-yl] ethoxy]phenyl methylene]thiazolidin-2,4-dione and its salts;

5-[4-[2-[1-Oxo-1,2-dihydro-phthalazin-2-yl]ethoxy]phenyl methylene]thiazolidin-2,4-dione and its salts;

5-[4-[2-[4-Ethyl-1-oxo-1,2-dihydro-phthalazin-2-yl] ethoxy]phenyl methylene]thiazolidin-2,4-dione and its salts;

5-[4-[2-[4-Phenyl-1-oxo-1,2-dihydro-phthalazin-2-yl] ethoxy]phenyl methylene]thiazolidin-2,4-dione and its salts;

5-[4-[[2-Methyl-1-oxo-1,2-dihydro-phthalazin-4-yl] methoxy]phenyl methylene]thiazolidin-2,4-dione and its salts;

5-[4-[2-[4-Methyl-1-oxo-1,2-dihydro-phthalazin-2-yl] ethoxy]phenyl methyl] thiazolidin-2,4-dione and its salts;

5-[4-[2-[1-Oxo-1,2-dihydro-phthalazin-2-yl]ethoxy]phenyl methyl]thiazolidin-2,4-dione and its salts;

5-[4-[2-[4-Ethyl-1-oxo-1,2-dihydro-phthalazin-2-yl] ethoxy]phenyl methyl]thiazolidin-2,4-dione and its salts;

5-[4-[2-[4-Phenyl-1-oxo-1,2-dihydro-phthalazin-2-yl] ethoxy]phenyl methyl]thiazolidin-2,4-dione and its salts;

5-[4-[[2-Methyl-1-oxo-1,2-dihydro-phthalazin-4-yl] methoxy]phenyl methyl]thiazolidin-2,4-dione and its salts;

5-[4-[2-[4-Oxo-3,4-dihydro-1H-2,3-benzoxazin-3-yl] ethoxy]phenyl methylene]thiazolidin-2,4-dione and its salts;

5-[4-[2-[4-Oxo-3,4-dihydro-1H-2,3-benzoxazin-3-yl] ethoxy]phenyl methyl]thiazolidin-2,4-dione and its salts;

5-[4-[2-[4-Hydroxy-1-oxo-1,2-dihydro-phthalazin-2-yl] ethoxy]phenyl methylene]thiazolidin-2,4-dione and its salts; and 5-[4-[2-[4-Hydroxy-1-oxo-1,2-dihydro-phthalazin-2-yl] ethoxy]phenyl methyl]thiazolidin-2,4-dione and its salts.

According to a feature of the present invention, there is provided a novel intermediate of the general formula (III)

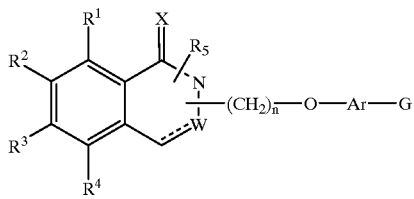

(III)

where X represents O or S; the group $R^1$, $R^2$, $R^3$, $R^4$ may be same or different and represent hydrogen, halogen, hydroxy, cyano, nitro; optionally substituted groups selected from alkyl, cycloalkyl, alkoxy, cycloalkyloxy, aryl, aralkyl, heteroaryl, heteroaralkyl, heterocyclyl, aryloxy, alkoxycarbonyl, aryloxycarbonyl, aralkoxycarbonyl, arylamino, amino group, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; "---" represents a bond or no bond; W represents oxygen atom or nitrogen atom, with the provision that when W represents nitrogen atom; "----" represents a bond and when W represents a oxygen atom "----" represents no bond; when $R^5$ is present on carbon atom, it represents hydrogen, hydroxy, halogen, nitro, cyano, optionally substituted groups selected from amino, alkyl, cycloalkoxy, cycloalkyl, acylamino, aryl, aralkyl, heterocyclyl, heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl groups, alkylamino, arylamino, alkoxycarbonylamino, aryloxycarbonylamino, aralkoxycarbonylamino, carboxylic acid and its derivatives, sulfonic acid and its derivatives; when $R^5$ is present on a nitrogen atom, it represents hydrogen, optionally substituted groups selected from alkyl, cycloalkyl, aryl, aralkyl, heterocyclyl, heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl groups, carboxylic acid derivatives, sulfonic acid derivatives; n is an integer ranging from 1–4; Ar represents an optionally substituted divalent aromatic or heterocyclic group; G represents —CHO, —NO$_2$, —NH$_2$ or —CH$_2$CH (J)—COOR, where J represents halogen atom such as chlorine, bromine or iodine and R represents H or lower alkyl group. The lower alkyl group may be a ($C_1$–$C_6$)alkyl group, preferably a ($C_1$–$C_3$)alkyl group such as methyl, ethyl or propyl.

According to a feature of the present invention, there is provided a process for the preparation of novel intermediate of the general formula (III)

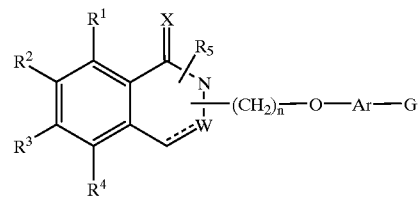

(III)

where $R^1$, $R^2$, $R^3$, $R^4$, $R^5$, X, W, n, and Ar are as defined earlier and G represents —CHO or —NO$_2$ group which comprises: reacting a compound of the general formula (IV)

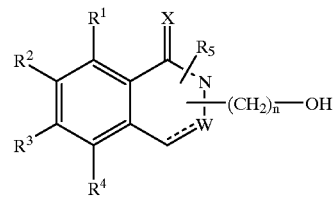

(IV)

where $R^1$, $R^2$, $R^3$, $R^4$, $R^5$, X, W, and n are as defined earlier, with a compound of general formula (V)

L$^1$—Ar—G  (V)

where L$^1$ is a halogen atom such as fluorine or chlorine, G is a CHO or a NO$_2$ group and Ar is as defined earlier.

The reaction of a compound of formula (IV) with a compound of formula (V) to produce a compound of formula (III) may be carried out in the presence of solvents such as THF, DMF, DMSO, DME and the like or mixtures thereof. The inert atmosphere may be maintained by using inert gases such as N$_2$, Ar or He. The reaction may be effected in the presence of a base such as K$_2$CO$_3$, Na$_2$CO$_3$, NaH and the like. Mixture of bases may be used. The reaction temperature may range from 20° C. to 150° C., preferably at a temperature in the range of 30° C. to 100° C. The duration of the reaction may range from 1 to 24 hours, preferably from 2 to 6 hours.

In another embodiment of the present invention, the novel intermediate of general formula (III), where G is a CHO or $NO_2$ group, can also be prepared by the reaction of compound of general formula (VI)

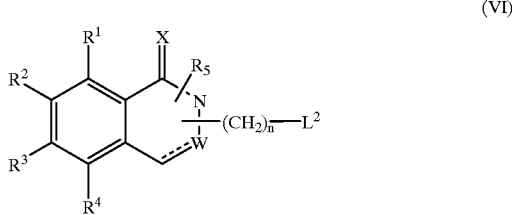

(VI)

where $R^1$, $R^2$, $R^3$, $R^4$, $R^5$, X, W, and n are as defined earlier and $L^2$ may be a halogen atom such as Cl, Br, I or a leaving group such as methanesulfonate, trifluoromethanesulfonate, p-toluenesulfonate with a compound of general formula (VII)

(VII)

where G is a CHO or $NO_2$ group and Ar is as defined earlier.

The reaction of a compound of formula (VI) with a compound of formula (VII) to produce a compound of the formula (III) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. The reaction temperature may range from 20° C.–120° C., preferably at a temperature in the range of 30° C.–100° C. The duration of the reaction may range from 1–12 hours, preferably from 2 to 6 hours.

In yet another embodiment of the present invention, the novel intermediate of general formula (III), where G is CHO or $NO_2$ group can also be prepared by the reaction of compound of general formula (VIII)

(VIII)

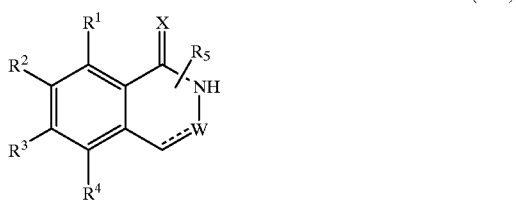

where $R^1$, $R^2$, $R^3$, $R^4$, $R^5$, X and W are as defined earlier, with the compound of formula (IX)

(IX)

where $L^2$, n, Ar and G are as defined earlier.

The reaction of a compound of formula (VIII) with a compound of formula (IX) to produce a compound of the formula (III) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof The reaction temperature may range from 20° C.–120° C., preferably at a temperature in the range of 30° C.–100° C. The duration of the reaction may range from 1–48 hours, preferably from 2 to 24 hours.

Alternatively, a compound of general formula (III) can also be prepared by the reaction of compound of general formula (IV) defined earlier with a compound of general formula (VII) defined earlier.

The reaction of compound of general formula (IV) with a compound of general formula (VII) may be carried out using suitable coupling agents such as dicyclohexyl urea, triarylphosphine/dialkylazadicarboxylate such as $PPh_3$/ DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

The present invention provides a process for the preparation of novel azolidinedione derivatives of general formula (I), their tautomeric forms, their stereoisomers, their polymorphs, their pharmaceutically acceptable salts and their pharmaceutically acceptable solvates wherein $R^1$, $R^2$, $R^3$, $R^4$, $R^5$, X, W, n, Ar and B are as defined earlier and $R^6$ together with $R^7$ represent a bond which comprises:

reacting the novel intermediate of the general formula (III) obtained above where G represents CHO group with 2,4-thiazolidinedione or 2,4-oxazolidinedione and removing the water formed during the reaction by conventional methods to yield a compound of general formula (X)

(X)

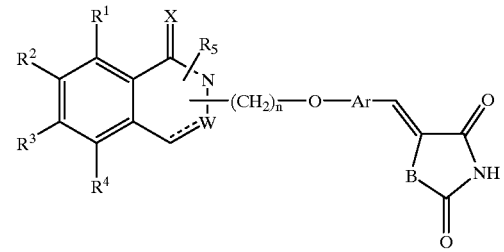

where $R^1$, $R^2$, $R^3$, $R^4$, $R^5$, X, W, n, Ar are as defined earlier and B represents sulfur or oxygen.

The reaction of the compound of the general formula (III) where G is a CHO group with 2,4-thiazolidinedione or 2,4-oxazolidinedione, to yield compound of general formula (X), wherein B represents a sulfur or an oxygen atom respectively, may be carried out neat in the presence of sodium acetate or in the presence of a solvent such as benzene, toluene, methoxyethanol or mixtures thereof. The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular seives. Oxazolidine-2-oxo-4-thione may be used instead of 2,4-oxazolidinedione, wherein the thio group may be converted to oxo group by oxidation using agents such as hydrogen peroxide or peroxyacids like mCPBA.

The compound of the general formula (X) obtained above is converted into its pharmaceutically acceptable salts, or its pharmaceutically acceptable solvates by conventional methods.

The compound of the general formula (X) obtained in the manner described above is reduced by known methods to obtain the compound of general formula (XI).

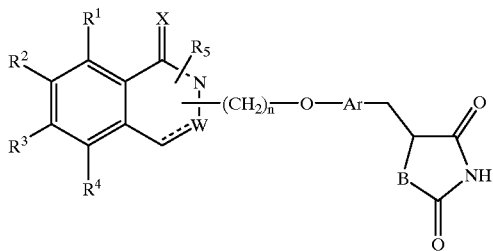

(XI)

wherein $R^1$, $R^2$, $R^3$, $R^4$, $R^5$, W n, Ar and B are as defined earlier. The compound of general formula (XI) represents the compound of general formula (I), wherein $R^6$ and $R^7$ represents hydrogen atom and other symbols are as defined earlier.

The reduction of compound of the formula (X) to yield a compound of the general formula (XI) may be carried out in the presence of gaseous hydrogen and a catalyst such as Pd/C, Rh/C, Pt/C, Raney Nickel, and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like in the presence of cobalt salt such as $CoCl_2$ and ligands, preferably bidentated ligands such as 2,2'-bipyridyl, 1,10-phenanthroline, bisoximes and the like.

The compound of the general formula (XI) obtained above is converted into its pharmaceutically acceptable salts, or its pharmaceutically acceptable solvates by conventional methods.

In yet another embodiment of the present invention, the compound of the general formula (I) can also be prepared by reacting a compound of the general formula (VI) defined above with a compound of general formula (XII)

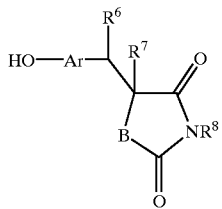

(XII)

where $R^6$, $R^7$, B and Ar are as defined earlier and $R^8$ is hydrogen or a nitrogen protecting group which is removed after the reaction.

The reaction of compound of formula (VI) with compound of formula (XII) to produce a compound of the formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as $K_2CO_3$, $Na_2CO_3$ or NaH or mixtures thereof. The reaction temperature may range from 20° C.–150° C., preferably at a temperature in the range of 30° C.–80° C. The duration of the reaction may range from 1–12 hours, preferably from 2 to 6 hours.

Alternatively, compound of the general formula (I) can also be prepared by reacting a compound of general formula (IV) defined earlier with a compound of general formula (XII) defined above.

The reaction of compound of general formula (IV) with a compound of general formula (XII) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of the present invention, the compound of general formula (I), where $R^1$, $R^2$, $R^3$, $R^4$, $R^5$, X, W, n, Ar are as defined earlier and $R^6$ and $R^7$ represents hydrogen atom, B represents S can be prepared by the reaction of compound of general formula (XIII)

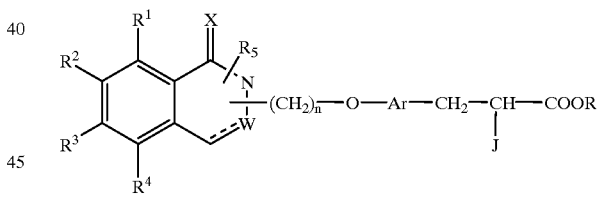

(XIII)

where $R^1$, $R^2$, $R^3$, $R^4$, $R^5$, X, W, n, Ar are as defined earlier, J is a halogen atom like chlorine, bromine or iodine and R is a lower alkyl group with thiourea followed by treatment with an acid.

The reaction of compound of general formula (XIII) with thiourea is normally carried out in the presence of alcoholic solvent such as methanol, ethanol, propanol, isobutanol, 2-methoxybutanol and the like or DMSO or sulfolane. The reaction may be conducted at a temperature in the range between 20° C. and the reflux temperature of the solvent used. Bases such as NaOAc, KOAc, NaOMe, NaOEt and the like may be used. The reaction is normally followed by treatment with a mineral acid such as hydrochloric acid at 20° C.–100° C.

The compound of general formula (XIII) where all the symbols are as defined earlier can be prepared by the diazotization of the amino compound of the general formula (XIV)

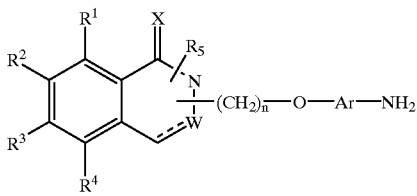

(XIV)

where all symbols are as defined earlier, using alkali metal nitrites followed by treatment with acrylic acid esters in the presence of hydrohalo acids and catalytic amount of copper oxide or copper halide.

The compound of general formula (XIV) can in turn be prepared by the conventional reduction of the novel intermediate (III) where G is $NO_2$ group and other symbols are as defined earlier.

In still another embodiment of the present invention the compound of general formula (I) may be prepared by reacting a compound of general formula (VIII) defined above with a compound of general formula (XV)

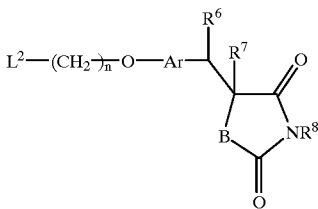

(XV)

where $L^2$, n, Ar, $R^6$, $R^7$, B are as defined earlier and $R^8$ is hydrogen or a nitrogen protecting group which is removed after the reaction.

The reaction of a compound of formula (VIII) with a compound of formula (XV) to produce a compound of the formula (III) may be carried out in the presence of solvents such as THF, DMF, DMSO, DME and the like or mixtures thereof The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. The reaction temperature may range from 20° C.–120° C., preferably at a temperature in the range of 30° C.–100° C. The duration of the reaction may range from 1–12 hours, preferably from 2 to 6 hours.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

As used in this application the term neat means the reaction is carried out without the use of solvent.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention also provides a pharmaceutical composition, containing compounds of the general formula (I), as defined above, their derivatives, their analogues, their tautomeric forms, their stereoisomers, their polymorphs, their pharmaceutically acceptable salts, their pharmaceutically acceptable solvates or mixtures thereof in combination with the usual pharmaceutically employed carriers, diluents and the like, useful for the treatment and/or prophylaxis of hyperlipemia, hypercholesterolemia, hyperglycemia, osteoporosis, obesity, glucose intolerance, insulin resistance and also diseases or conditions in which insulin resistance is the underlying pathophysiological mechanism such as type II diabetes, impaired glucose tolerance, dyslipidaemia, hypertension, coronary heart disease and other cardiovascular disorders including atherosclerosis; insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents, excipients, or solvents.

A typical tablet production method is exemplified below:

Tablet Production Example:

| a) | 1) Active ingredient | 30 g |
|---|---|---|
| | 2) Lactose | 95 g |
| | 3) Corn starch | 30 g |

| | | |
|---|---|---|
| 4) Carboxymethyl cellulose | 44 g | |
| 5) Magnesium stearate | 1 g | |
| | 200 g for 1000 tablets | |

The ingredients 1 to 3 are uniformly blended with water and granulated after drying under reduced pressure. The ingredient 4 and 5 are mixed well with the granules and compressed by a tabletting machine to prepare 1000 tablets each containing 30 mg of active ingredient.

| | | |
|---|---|---|
| b) 1) Active ingredient | 10 g | |
| 2) Calcium phosphate | 90 g | |
| 3) Lactose | 50 g | |
| 4) Corn starch | 45 g | |
| 5) Polyvinyl pyrrolidone | 3.5 g | |
| 6) Magnesium stearate | 1.5 g | |
| | 200 g for 1000 tablets | |

The ingredients 1–4 are uniformly moistened with an aqueous solution of ingredient 5 and granulated after drying under reduced pressure. Ingredient 6 is added and granules are compressed by a tabletting machine to prepare 1000 tablets containing 10 mg of ingredient 1.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 mg to about 200 mg/kg body weight of the subject per day or preferably about 0.10 mg to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

4-[[2-Methyl-1-oxo-1,2-dihydro-phthalazin-4-yl]methoxy]benzaldehyde:

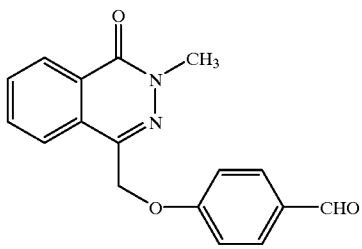

To a stirred solution of 4-hydroxymethyl-2-methyl-1(2H)-pthalazinone (350 mg, 1.84 mmol) (prepared according to the procedure described in Chem. Pharm. Bull., 28 (1980) 2763) in dry DMF (30 mL) was added NaH (88 mg, 3.68 mmol) in portions over 30 min at 25–30° C., followed by 4-fluorobenzaldehyde (228 mg, 1.84 mmol) added dropwise, keeping the temperature between 0–15° C. The reaction mixture was stirred at room temperature further for 6 h. Ice (200 g) was added to the reaction mixture and extracted with EtOAc. The EtOAc layer was washed with water, dried over anhydrous $Na_2SO_4$ and concentrated to obtain the title compound (300 mg, 50%). mp: 168–170° C.

$^1$H NMR ($CDCl_3$): δ9.92 (s, 1H), 8.48 (d, J=8.10 Hz, 1H), 8.0–7.72 (m, 5H), 7.18 (d, J=8.72 Hz, 2H), 5.39 (s, 2H), 3.88 (s, 3H).

Preparation 2

4-[2-[4-Methyl-1-oxo-1,2-dihydro-phthalazin-2-yl]ethoxy]benzaldehyde:

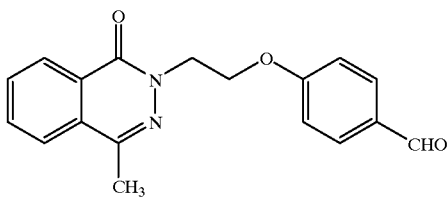

To a stirred suspension of $K_2CO_3$ (11.3 g, 82.5 mmol) in dry DMF (50 mL) at 25–30° C. was added a solution of 4-methyl-1(2H)-phthalazinone (6.6 g, 41.25 mmol) (Ref: Chemistry of Heterocyclic Compounds; Condensed Pyridazines including Cinnolines and Phthalazines, edited by R. N. Castle; John Wiley and Sons, 27, (1973) 375–441) in dry DMF (100 mL). The reaction mixture was stirred for 30 min at 25° C. and 4-(2-bromoethoxy)benzaldehyde (9.4 g, 41.25 mmol) was added. The reaction mixture was immersed in a pre-heated oil bath at 70° C. and stirred at 65–70° C. for 24 h. The reaction mixture was cooled to room temperature and water (50 mL) was added. The reaction mixture was extracted with EtOAc (3×50 mL). The combined organic layers were washed with brine, dried over anhydrous $Na_2SO_4$ and concentrated. The crude compound was recrystallised from methanol to obtain the title compound (9.7 g, 77%). mp: 90° C.

$^1$H NMR ($CDCl_3$): δ9.85 (s, 1H), 8.46 (d, J=8.10 Hz, 1H), 7.90–7.20 (m, 5H), 7.03 (d, J=8.50 Hz, 2H), 4.64 (t, J=5.66 Hz, 2H), 4.50 (t, J=5.66 Hz, 2H), 2.50 (s, 3H).

Preparation 3

4-[2-[1-Oxo-1,2-dihydro-phthalazin-2-yl]ethoxy]benzaldehyde:

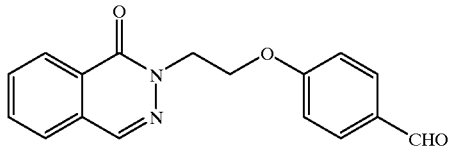

The title compound (700 mg, 44%) was prepared from 1(2H)-phthalazinone (800 mg, 5.48 mmol) (Ref: Chemistry of Heterocyclic Compounds; Condensed Pyridazines including Cinnolines and Phthalazines, edited by R. N. Castle; John Wiley and Sons, 27, (1973) 375–441), 4-[2-bromoethoxy]benzaldehyde (1.25 g, 5.48 mmol) and $K_2CO_3$ (1.5 g, 10.96 mmol) by a similar procedure to that described in preparation 2. mp: 104–106° C.

$^1$H NMR ($CDCl_3$): δ9.87 (s, 1H), 8.46 (d, J=8.10 Hz, 1H), 8.19 (s, 1H), 7.87–7.69 (m, 5H), 7.04 (d, J 8.72 Hz, 2H), 4.69 (t, J=5.70 Hz, 2H), 4.53 (t, J=5.70 Hz, 2H).

Preparation 4

4-[2-[4-Ethyl-1-oxo-1,2-dihydro-phthalazin-2-yl]ethoxy]benzaldehyde:

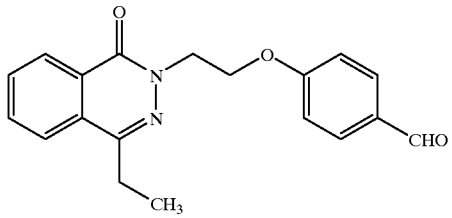

The title compound (450 mg, 54%) was prepared from 4-ethyl-1(2H)-phthalazinone (450 mg, 2.6 mmol) (Ref: Chemistry of Heterocyclic Compounds; Condensed Pyridazines including Cinnolines and Phthalazines, edited by R. N. Castle; John Wiley and Sons, 27, (1973) 375–441), 4-[2-bromoethoxy]benzaldehyde (600 mg, 2.6 mmol) and $K_2CO_3$ (720 mg, 5.2 mmol) by a similar procedure to that described in preparation 2. mp: 110° C.

$^1$H NMR ($CDCl_3$): δ9.91 (s, 1H), 8.51 (d, J=8.10 Hz, 1H), 7.92–7.70 (m, 5H), 7.02 (d, J=8.72 Hz, 2H), 4.68 (t, J=5.70 Hz, 2H), 4.50 (t, J=5.70 Hz, 2H), 2.98 (q, J=7.05 Hz, 2H), 1.36 (t, J=7.05 Hz, 3H).

Preparation 5

4-[2-[4-Phenyl-1-oxo-1,2-dihydro-phthalazin-2-yl]ethoxy]benzaldehyde:

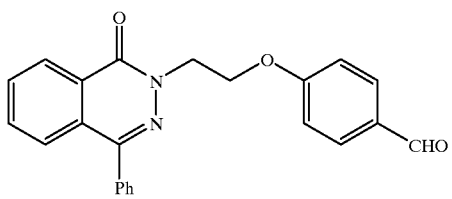

The title compound (2.0 g, 85%) was obtained from 4-phenyl-1(2H)-phthalazinone (1.30 g, 5.85 mmol) (prepared according to the procedure described in *J. Med. Chem.*, 36 (1993) 4052), 4-(2-bromoethoxy)benzaldehyde (1.34 g, 5.85 mmol) and $K_2CO_3$ (1.6 g, 11.7 mmol) by a similar procedure to that described in preparation 2. mp: 136° C.

$^1$H NMR ($CDCl_3$): δ9.86 (s, 1H), 8.55 (d, J=8.10 Hz, 1H), 7.85–7.65 (m, 5H), 7.55 (bs, 5H), 7.03 (d, J=8.72 Hz, 2H), 4.75 (t, J=5.70 Hz, 2H), 4.56 (t, J=5.70 Hz, 2H).

Preparation 6

4-[2-[4-Oxo-3,4-dihydro-1H-2,3-benzoxazin-3-yl]ethoxy]benzaldehyde:

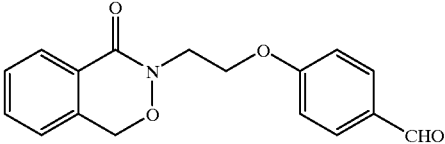

The title compound (370 mg, 66%) was prepared from 4-oxo-3,4-dihydro-1H-2,3-benzoxazine (280 mg, 1.87 mmol) (prepared according to the procedure described in *Tetrahedron*, 22 (1966) 2107) and 4-(2-bromoethoxy)benzaldehyde (430 mg, 1.87 mmol) and $K_2CO_3$ (520 mg, 3.74 mmol). mp: 102° C.

$^1$H NMR ($CDCl_3$): δ9.89 (s, 1H), 8.10 (d, J=7.20 Hz, 1H), 7.80 (d, J=8.70 Hz, 2H), 7.60–7.40 (m, 2H), 7.10 (d, J=7.0 Hz, 1H), 7.04 (d, J=8.70 Hz, 2H), 5.11 (s, 2H), 4.35 (t, J=5.0 Hz, 2H), 4.23 (t, J=5.0 Hz, 2H).

Preparation 7

4-[2-[4-Hydroxy-1-oxo-1,2-dihydro-phthalazin-2-yl]ethoxy]benzaldehyde:

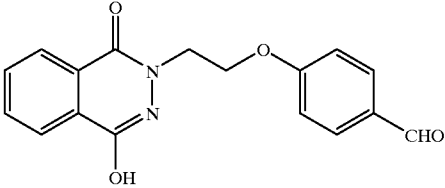

To a stirred suspension of NaH (76 mg, 3.0 mmol, 95%) in dry DMF (10 mL) was added 2,3-dihydropthalazine-1,4-dione (486 mg, 3.0 mmol) (prepared according to the procedure described in *Bull. Soc. Chim. Belges.*, 74 (1965) 91–100) at 25–30° C. and immersed in a preheated oil bath at 60° C. and stirred for 30 min at 60° C. A solution of 4-(2-bromoethoxy)benzaldehyde (636 mg, 3.0 mmol) in dry DMF (3 mL) was added dropwise and stirred further for 12 h at 60° C. The reaction mixture was cooled to room temperature and water (15 mL) was added. The reaction mixture was extracted with EtOAc (3×10 mL). The combined organic layers were washed with brine, dried over anhydrous $Na_2SO_4$ and concentrated. The crude compound was chromatographed on silicagel using EtOAc: pet. ether (1:2) as eluent to obtain the title compound (465 mg, 48%).

$^1$H NMR ($CDCl_3$): δ10.05 (s, 1H, $D_2O$ exchangable), 9.91 (s, 1H), 8.48–8.32 (m, 1H), 8.08–7.92 (m, 1H), 7.92–7.65 (m, 4H), 7.08 (d, J 8.68 Hz, 2H), 4.71 (t, J=4.56 Hz, 2H), 4.49 (t, J=4.56 Hz, 2H).

EXAMPLE 1
5-[4-[2-[4-Methyl-1-oxo-1,2-dihydro-phthalazin-2-yl]ethoxy]phenyl methylene]thiazolidin-2,4-dione:

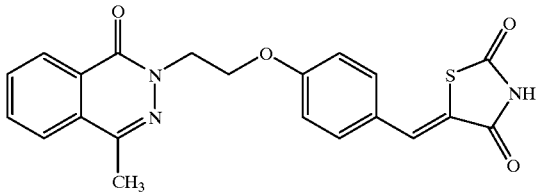

A mixture of 4-[2-[4-methyl-1-oxo-1,2-dihydro-phthalazin-2-yl]ethoxy]benzaldehyde (2.75 g, 8.93 mmol) obtained in preparation 2, thiazolidin-2,4-dione (1.05 g, 8.93 mmol), benzoic acid (0.15 g, 1.23 mmol) and piperidine (0.14 mL, 1.42 mmol) in toluene (125 mL) was refluxed for 2 h with continuous removal of water. The reaction mixture was cooled to room temperature and the resultant crystalline compound was filtered; washed with water and dried under reduced pressure to obtain the title compound (3.3 g, 91%). mp: 202° C.

$^1$H NMR (DMSO-d$_6$): δ8.49 (d, J=8.10 Hz, 1H), 7.90–7.75 (m, 3H), 7.72 (s, 1H), 7.40 (d, J=8.30 Hz, 2H), 6.95 (d, J=8.30 Hz, 2H), 4.55 (t, J=5.30 Hz, 2H), 4.48 (t, J=5.30 Hz, 2H), 2.60 (s, 3H).

EXAMPLE 2
5-[4-[2-[1-Oxo-1,2-dihydro-phthalazin-2-yl]ethoxy]phenyl methylene]thiazolidin-2,4-dione:

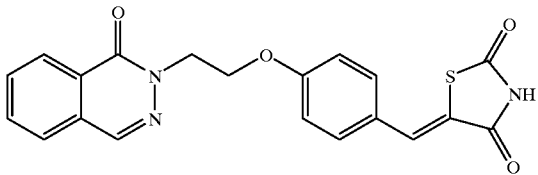

The title compound (533 mg, 80%) was prepared from 4-[2-[1-oxo-1,2-dihydro-phthalazin-2-yl]ethoxy]benzaldehyde (500 mg, 1.7 mmol) obtained from preparation 3 and thiazolidin-2,4-dione (200 mg, 1.7 mmol) by an analogous procedure to that described in example 1. mp: 242° C.

$^1$H NMR (DMSO-d$_6$+CDCl$_3$): δ12.32 (bs, 1H, D$_2$O exchangeable), 8.35 (s, 1H), 8.33 (d, J=7.20 Hz, 1H), 8.06 (s, 1H), 7.98–7.88 (m, 3H), 7.46 (d, J=8.72 Hz, 2H), 7.05 (d, J=8.72 Hz, 2H), 4.58 (t, J=5.25 Hz, 2H), 4.50 (t, J=5.2 Hz, 2H).

EXAMPLE 3
5-[4-[2-[4-Ethyl-1-oxo-1,2-dihydro-phthalazin-2-yl]ethoxy]phenyl methylene]thiazolidin-2,4-dione:

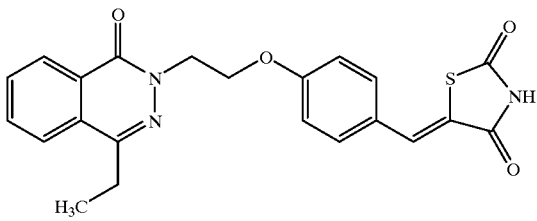

The title compound (432 mg, 83%) was prepared from 4-[2-[4-ethyl-1-oxo-1,2-dihydro-phthalazin-2-yl]ethoxy]benzaldehyde (400 mg, 1.24 mmol) obtained from preparation 4 and thiazolidin-2,4-dione (145 mg, 1.24 mmol) by an analogous procedure to that described in example 1. mp: 230° C.

$^1$H NMR (DMSO-d$_6$+CDCl$_3$): δ12.34 (bs, 1H, D$_2$O exchangeable), 8.35 (d, J=7.15 Hz, 1H), 8.09 (s, 1H), 7.98–7.80 (m, 3H), 7.45 (d, J=8.72 Hz, 2H), 7.04 (d, J=8.72 Hz, 2H), 4.65–4.38 (m, 4H), 2.98 (q, J=7.38 Hz, 2H), 1.31 (t, J=7.38 Hz, 3H).

EXAMPLE 4
5-[4-[2-[4-Phenyl-1-oxo-1,2-dihydro-phthalazin-2-yl]ethoxy]phenyl methylene]thiazolidin-2,4-dione:

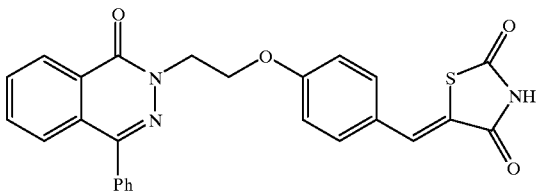

The title compound (1.1 g, 87%) was prepared from 4-[2-[4-phenyl-1-oxo-1,2-dihydro-phthalazin-2-yl]ethoxy]benzaldehyde (1.00 g, 2.7 mmol) obtained from preparation 5 and 2,4-thiazolidinedione (316 mg, 2.7 mmol) by a similar procedure to that described in example 1. mp: 224° C.

$^1$H NMR (CDCl$_3$+DMSO-d$_6$): δ12.20 (bs, 1H, D$_2$O exchangeable), 8.45 (t, J=7.30 Hz, 1H), 7.96 (s, 1H), 7.89–7.60 (m, 3H), 7.60–7.40 (m, 5H), 7.44 (d, J=8.72 Hz, 2H), 7.04 (d, J=8.72 Hz, 2H), 4.65 (t, J=5.25 Hz, 2H), 4.55 (t, J=5.2 Hz, 2H).

EXAMPLE 5
5-[4-[[2-Methyl-1-oxo-1,2-dihydro-phthalazin-4-yl]methoxy]phenyl methylene]thiazolidin-2,4-dione:

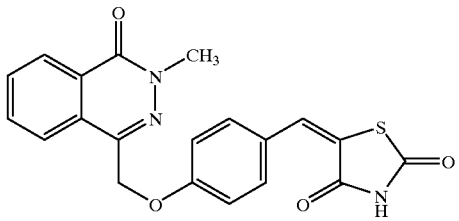

The title compound (250 mg, 98%) was prepared from 4-[2-methyl-1-oxo-1,2-dihydro-phthalazin-4-yl]methoxy]benzaldehyde (190 mg, 0.65 mmol) obtained in preparation 1 and 2,4-thiazolidinedione (75 mg, 0.65 mmol) by an analogous procedure to that described in example 1. mp: 262° C.

$^1$H NMR (CDCl$_3$+DMSO-d$_6$): δ8.35 (d, J=7.25 Hz, 1H), 8.15–7.90 (m, 3H), 7.70 (s, 1H), 7.62 (d, J=8.72 Hz, 2H), 7.28 (d, J=8.72 Hz, 2H), 5.47 (s, 2H), 3.79 (s, 3H).

EXAMPLE 6
5-[4-[2-[4-Methyl-1-oxo-1,2-dihydro-phthalazin-2-yl]ethoxy]phenyl methyl] thiazolidin-2,4-dione:

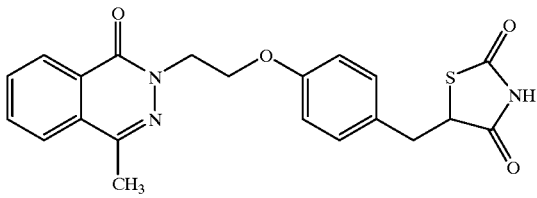

A solution of 5-[4-[2-[4-methyl-1-oxo-1,2-dihydro-phthalazin-2-yl]ethoxy]phenyl methylene] thiazolidin-2,4-dione (9.0 g, 22.0 mmoles) obtained in example 1, in 1,4-dioxane (500 mL) was reduced with hydrogen in the presence of 10% palladium on charcoal (22.5 g) at 60 psi for 48 h. The mixture was filtered through a bed of celite. The filtrate was evaporated to dryness under reduced pressure. The crude compound was recrystallised using $CH_2Cl_2$/pet. ether to afford the title compound (7.2 g, 80%). mp: 170° C.

$^1$H NMR (CDCl$_3$): δ8.51 (d, J=8.10 Hz, 1H), 7.91–7.68 (m, 3H), 7.11 (d, J=8.50 Hz, 2H), 6.88 (d, J=8.50 hz, 2H), 4.61 (t, J=6.10 Hz, 2H), 4.46 (dd, J=9.50, 3.70 Hz, 1H), 4.40 (t, J=6.10 Hz, 2H), 3.42 (dd, J=14.12, 3.70 Hz, 1H), 3.07 (dd, J=14.12, 9.50 Hz, 1H), 2.60 (s, 3H).

EXAMPLE 7
5-[4-[2-[1-Oxo-1,2-dihydro-phthalazin-2-yl]ethoxy]phenyl methyl]thiazolidin-2,4-dione:

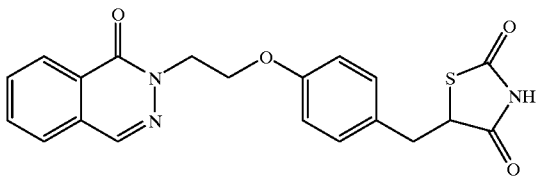

The title compound (200 mg, 52%) was prepared from 5-[4-[2-[1-oxo-1,2-dihydro-phthalazin-2-yl]ethoxy]phenyl methylene]thiazolidin-2,4-dione (385 mg, 0.98 mmol) obtained in example 2, by a similar procedure to that described in example 6. mp: 165° C.

$^1$H NMR (CDCl$_3$): δ8.45 (d, J=8.62 Hz, 1H), 8.20 (s, 1H), 8.07 (bs, 1H, D$_2$O exchangeable), 7.90–7.60 (m, 3H), 7.11 (d, J=8.72 Hz, 2H), 6.88 (d, J=8.72 Hz, 2H), 4.65 (t, J=5.81 Hz, 2H), 4.46 (dd, J=9.32 and 3.97 Hz, 1H), 4.42 (t, J=5.81 Hz, 2H), 3.40 (dd, J=14.12 and 3.97 Hz, 1H), 3.08 (dd, J=14.12 and 9.32 Hz, 1H).

EXAMPLE 8
5-[4-[2-[4-Ethyl-1-oxo-1,2-dihydro-phthalazin-2-yl]ethoxy]phenyl methyl]thiazolidin-2,4-dione:

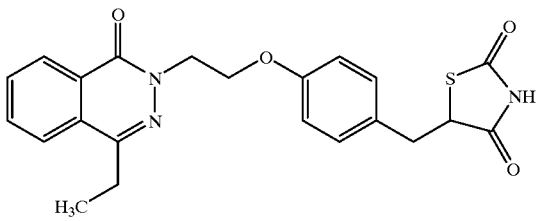

The title compound (200 mg, 46%) was prepared from 5-[4-[2-[4-ethyl-1-oxo-1,2-dihydro-phthalazin-2-yl]ethoxy] phenyl methylene]thiazolidin-2,4-dione (430 mg, 1.02 mmol) obtained in example 3 by a similar procedure to that described in example 6. mp: 174° C.

$^1$H NMR (CDCl$_3$): δ8.46 (d, J=8.41 Hz, 1H), 8.02 (bs, 1H, D$_2$O exchangeable), 7.80–7.60 (m, 3H), 7.08 (d, J=8.72 Hz, 2H), 6.85 (d, J=8.72 Hz, 2H), 4.59 (t, J=5.9 Hz, 2H), 4.42 (dd, J=9.59 and 3.92 Hz, 1H), 4.32 (t, J=5.90 Hz, 2H), 3.40 (dd, J=14.11 and 3.92 Hz, 1H), 3.04 (dd, J=14.11 and 9.59 Hz, 1H), 2.96 (q, J=7.50 Hz, 2H), 1.33 (t, J=7.50 Hz, 3H).

EXAMPLE 9
5-[4-[2-[4-Phenyl-1-oxo-1,2-dihydro--phthalazin-2-yl]ethoxy]phenyl methyl]thiazolidin-2,4-dione:

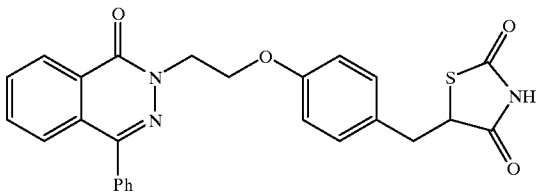

The title compound (600 mg, 60%) was prepared from 5-[4-[2-[[4-phenyl-1-oxo-1,2-dihydro-phthalazin-2-yl]ethoxy]phenyl methylene]thiazolidin-2,4-dione (1.0 g, 2.1 mmol) obtained in example 4, by a similar procedure to that described in example 6. mp: 198° C.

$^1$H NMR (CDCl$_3$): δ8.55 (d, J=8.30 Hz, 1H), 8.00 (bs, 1H, D$_2$O exchangeable), 7.90–7.70 (m, 3H), 7.70–7.45 (m, 5H), 7.11 (d, J=8.62 Hz, 2H), 6.89 (d, J=8.62 Hz, 2H), 4.72 (t, J=5.90 Hz, 2H), 4.46 (t, J=5.90 Hz, 2H), 4.42 (dd, J=9.6, 3.74 Hz, 1H), 3.44 (dd, J=14.12 and 3.74 Hz, 1H), 3.07 (dd, J=14.12, 9.6 Hz, 1H).

EXAMPLE 10
5-[4-[[2-Methyl-1-oxo-1,2-dihydro-phthalazin-4-yl]methoxy]phenyl methyl]thiazolidin-2,4-dione:

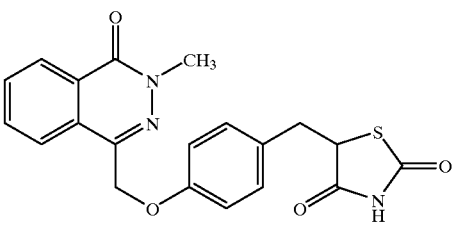

The title compound (0.5 g, 50%) was obtained from 5-[4-[2-methyl-1-oxo-1,2-dihydro-phthalazin-4-yl]methoxy]phenyl methylene]thiazolidin-2,4-dione (1.0 g, 2.54 mmol) obtained in example 5, by a similar procedure to that described in example 6. mp: 234° C.

$^1$H NMR (CDCl$_3$+DMSO-d$_6$): δ11.70 (bs, 1H, D$_2$O exchangeable), 8.42 (d, J=7.30 Hz, 1H), 7.99 (d, J=7.30 Hz, 1H), 7.92–7.88 (m, 2H), 7.19 (d, J=8.12 Hz, 2H), 6.99 (d, J=8.12 Hz, 2H), 5.28 (s, 2H), 4.46 (dd, J=9.44, 3.74 Hz, 1H), 3.86 (s, 3H), 3.46 (dd, J=14.11, 3.74 Hz, 1H), 3.08 (dd, J=14.11, 9.44 Hz, 1H).

EXAMPLE 11
5-[4-[2-[4-Oxo-3,4-dihydro-1H-2,3-benzoxazin-3-yl]ethoxy]phenyl methylene]thiazolidin-2,4-dione:

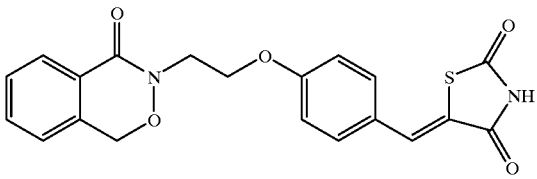

The title compound (310 mg, 67%) was obtained from 4-[2-[4-oxo-3,4-dihydro-1H-2,3-benzoxazin-3-yl]ethoxy]benzaldehyde (350 mg, 1.18 mmol), obtained in preparation 6, and thiazolidine-2,4-dione (138 mg, 1.18 mmol) by an analogous procedure to that described in example 1. mp: 192° C.

$^1$H NMR (CDCl$_3$): δ12.15 (bs, 1H, D$_2$O exchangeable), 8.02 (d, J=7.40 Hz, 1H), 7.71 (s, 1H), 7.60–7.50 (m, 2H), 7.44 (d, J=8.70 Hz, 2H), 7.20 (d, J=7.40 Hz, 1H), 7.04 (d, J=8.70 Hz, 2H), 5.14 (s, 2H), 4.35 (t, J=5.40 Hz, 2H), 4.18 (t, J=5.40 Hz, 2H).

EXAMPLE 12
5-[4-[2-[4-Oxo-3,4-dihydro-1H-2,3-benzoxazin-3-yl]ethoxy]phenyl methyl]thiazolidin-2,4-dione:

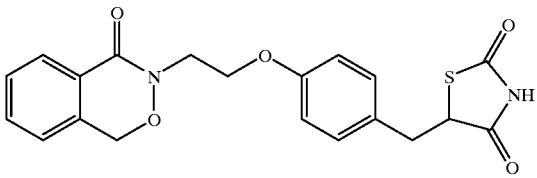

The title compound (100 mg, 40%) was obtained from 5-[4-[2-[4-oxo-3,4-dihydro-1H-benzoxazin-3-yl]ethoxy]phenyl methylene]thiazolidin-2,4-dione (250 mg, 0.63 mmol) obtained in example 11, by a similar procedure to that described in example 6. mp: 140° C.

$^1$H NMR (CDCl$_3$): δ8.08 (d, 7.20 Hz, 1H), 8.00 (bs, 1H, D$_2$O exchangable), 7.60–7.40 (m, 3H), 7.21 (d, J=8.60 Hz, 2H), 6.88 (d, J=8.60 Hz, 2H), 5.09 (s, 2H), 4.50 (dd, J=9.22, 3.83 Hz, 1H), 4.24 (t, J=4.50 Hz, 2H), 4.18 (t, J=4.5 Hz, 2H), 3.41 (dd, J=14.11, 3.73 Hz, 1H), 3.12 (dd, J=14.11, 4.89 Hz, 1H).

EXAMPLE 13
5-[4-[2-[4-Hydroxy-1-oxo-1,2-dihydro-phthalazin-2-yl]ethoxy]phenyl methylene] thiazolidin-2,4-dione:

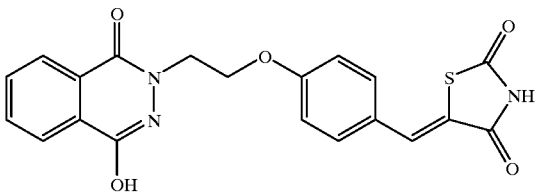

The title compound (150 mg, 75%) was prepared from 4-[2-[4-hydroxy-1-oxo-1,2-dihydro-phthalazin-2-yl]ethoxy]benzaldehyde (155 mg, 0.5 mmol) obtained from preparation 7 and 2,4-thiazolidinedione (70 mg, 0.5 mmol) by a similar procedure to that described in example 1. mp: 266–268° C.

$^1$H NMR (DMSO-d$_6$): δ11.98 (s, 1H, D$_2$O exchangeable), 8.25 (d, J=6.73 Hz, 1H), 8.02–7.92 (m, 3H), 7.70 (s, 1H), 7.59 (d, J=8.40 Hz, 2H), 7.22 (d, J=8.40 Hz, 2H), 4.60 (t, J=4.50 Hz, 2H), 4.53 (t, J=4.50 Hz, 2H).

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838 ; Annu. Rep. Sankyo Res. Lab. (1994) 46: 1–57). The homozygous animals, C$_{57}$ BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

The compounds of the present invention showed blood sugar and triglycerides lowering activities through improved insulin resistance. This was demonstrated by the following in vivo experiments.

Male C57BL/KsJ-db/db mice of 8 to 14 weeks age, having body weight range of 35 to 60 grams, procured from the Jackson Laboaotory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglycerides levels were measured spectrometrically, by glucose oxidase and glycerol-3-PO$_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose and administered to test group at a dose of 10 mg to 100 mg/kg through oral gavage daily for 6 days. The control group received vehicle (dose 10 ml kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/triglycerides lowering activity}(\%) = 1 - \frac{DT/DC}{TC/ZC} \times 100$$

ZC = Zero day control group value
DC = Zero day treated group value
TC = Control group value on test day
DT = Treated group value on the test day No adverse effects were observed for any of the mentioned compounds of invention in the above test. The compounds of the present invention also showed cholesterol lowering activity in the experimental animals used.

| Compound | Dose (mg/kg/day) | Maximum reduction in blood glucose level (%) | Triglyceride lowering (%) |
|---|---|---|---|
| Example 6 | 10 | 61 | 40 |
| Example 11 | 10 | 37 | 60 |

The experimental results from the db/db mice suggest that the novel compounds of the present invention also possess therapeutic utility as a prophylactic or regular treatment for obesity, cardiovascular disorders such as hypertension, hyperlipidaemia and other diseases; as it is known from the literature that such diseases are interrelated to each other.

We claim:

1. A compound of formula (I)

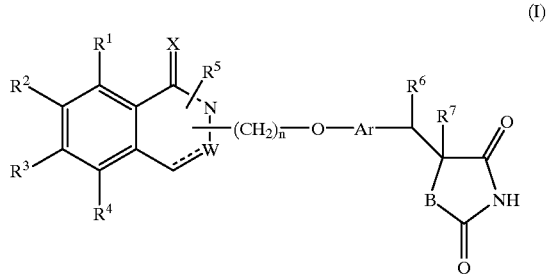

(I)

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro; or optionally substituted groups selected from alkyl, $(C_3–C_6)$cycloalkyl, alkoxy, cycloalkoxy, aryl, aralkyl, heteroaryl, heteroaralkyl, heterocyclyl wherein the heterocyclyl is selected from aziridinyl, pyrrolidinyl, morpholinyl, piperidinyl, or piperazinyl; aryloxy, alkoxycarbonyl, aralkoxycarbonyl, aryloxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its esters or amides; acyloxy, sulfonic acid or its esters or amides; "----" represents a bond; W represents a nitrogen atom; when $R^5$ is present on a carbon atom, it represents hydrogen, hydroxy, halogen, nitro, cyano or optionally substituted groups selected from amino, alkyl, $(C_3–C_6)$cycloalkyl, cycloalkoxy, acylamino, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its esters or amides, sulfonic acid and its esters or amides; when $R^5$ is present on a nitrogen atom, it represents hydrogen, or optionally substituted groups selected from alkyl, cycloalkyl, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, esters or amides of carboxylic acid, or esters or amides of sulfonic acid; n is an integer ranging from 1–4; Ar represents optionally substituted groups selected from divalent phenylene, naphthlene, pyridyl, quinolinyl, benzofuryl, dihydrobenzofuryl, benzopyranyl, indolyl, indolinyl, azaindolyl, azaindolinyl, pyrazolyl, benzothiazolyl, and benzoxazolyl; $R^6$ and $R^7$ are the same or different and individually represent hydrogen atom, hydroxy, halogen or lower alkyl group or together form a bond; and B represents an oxygen atom or a sulfur atom.

2. A compound as claimed in claim 1, wherein $R^1$, $R^2$, $R^3$, or $R^4$ are substituted and the substituents are selected from halogen, hydroxy, cyano or nitro or optionally substituted groups selected from alkyl, $(C_3–C_6)$cycloalkyl, alkoxy, cycloalkoxy, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl, alkoxycarbonylamino, aryloxycarbonylamino, aralkoxycarbonylamino, carboxylic acid or its esters or amides or sulfonic acid or its esters or amides.

3. A compound as claimed in claim 1, wherein the substituents on $R^5$ are selected from halogen, hydroxy, cyano or nitro, or optionally substituted groups selected from alkyl, $(C_3–C_6)$cycloalkyl, alkoxy, cycloalkoxy, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl, carboxylic acid or its esters or amides or sulfonic acid or its esters or amides.

4. A compound as claimed in claim 1, wherein the substituents on the group represented by Ar are selected from linear or branched $(C_1–C_6)$alkyl, $(C_1–C_3)$alkoxy, halogen, acyl, amino, acylamino, thio, or carboxylic or sulfonic acids or their esters or amides.

5. An intermediate of formula (III)

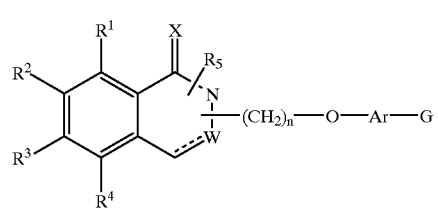

(III)

wherein X represents O or S; $R^1$, $R^2$, $R^3$, $R^4$, $R^5$, are the same or different and represent hydrogen, halogen, hydroxy, cyano, nitro; or optionally substituted groups selected from alkyl, $(C_3–C_6)$cycloalkyl, alkoxy, cycloalkoxy, aryl, aralkyl, heteroaryl, heteroaralkyl, heterocyclyl wherein the heterocyclyl is selected from aziridinyl, pyrrolidinyl, morpholinyl, piperidinyl, or piperazinyl; aryloxy, alkoxycarbonyl, aryloxycarbonyl, aralkyoxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its esters or amides, acyloxy, sulfonic acid or its esters or amides; "----" represents a bond; W represents a nitrogen atom; when $R^5$ is present on a carbon atom, it represents hydrogen, hydroxy, halogen, nitro, cyano, or optionally substituted groups selected from amino, alkyl, $(C_3–C_6)$cycloalkyl, cycloalkoxy, acylamino, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its esters or amides, sulfonic acid and its esters or amides; when $R^5$ is present on a nitrogen atom, it represents hydrogen or optionally substituted groups selected from alkyl, $(C_3–C_6)$cycloalkyl, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, carboxylic acid or its esters or amides, or sulfonic acid or its esters or amides; n is an integer ranging from 1–4; Ar represents optionally substituted groups selected from divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl, and benzoxazolyl; G represents CHO, $NO_2$, $—NH_2$ or $—CH_2CH(J)COOR$, where J represents a halogen atom and R represents H or lower alkyl group.

6. A process for the preparation of the intermediate of formula (III) as defined in claim 5, which comprises:

a) reacting a compound of formula (IV)

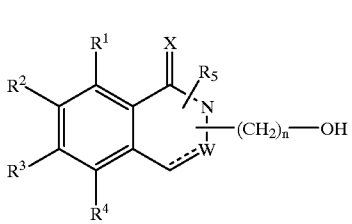
(IV)

wherein, $R^1$, $R^2$, $R^3$, $R^4$, $R^5$, X, W, and n are as defined in claim 5, with a compound of formula (V)

$L^1$—Ar—G     (V)

where $L^1$ is a halogen atom, G is a CHO or a $NO_2$ group and Ar is as defined in claim 5;

b) reacting a compound of formula (VI)

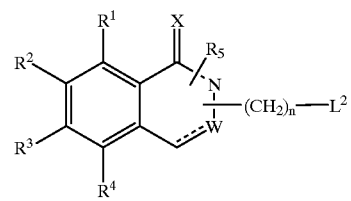
(VI)

where $R^1$, $R^2$, $R^3$, $R^4$, $R^5$, X, W, and n are as defined in claim 5 and $L^2$ is a halogen atom or a leaving group with a compound of formula (VII)

HO—Ar—G     (VII)

where G is a CHO or $NO_2$ group and Ar is as defined in claim 5;

c) reacting a compound of formula (IV)

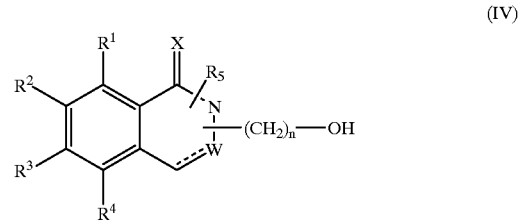
(IV)

wherein, $R^1$, $R^2$, $R^3$, $R^4$, $R^5$, X, W, and n are as defined in claim 5, with a compound of formula (VII)

HO—AR—G     (VII)

where G is a CHO or $NO_2$ group and Ar is as defined in claim 5;

d) reacting a compound of formula (VIII)

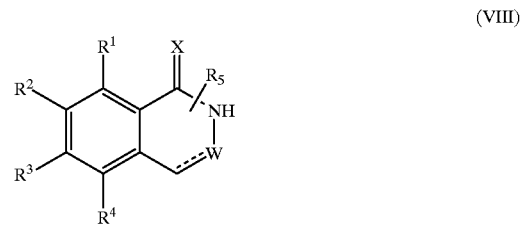
(VIII)

where $R^1$, $R^2$, $R^3$, $R^4$, $R^5$, X and W are as defined in claim 5, with a compound of formula (IX)

$L^2$—$(CH_2)_n$—O—Ar—G     (IX)

where n, Ar and G are as defined in claim 5 and $L^2$ is a leaving group; and (e) diazotizating a compound of formula (XIV)

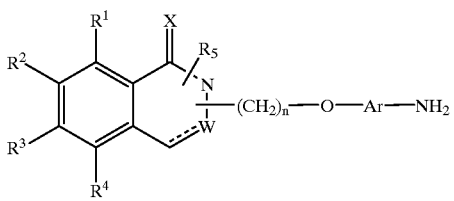

wherein, $R^1$, $R^2$, $R^3$, $R^4$, $R^5$, X, W, n, and Ar are as defined in claim 5, followed by treatment with acrylic acid ester in the presence of hydrohalo acids and copper oxide or copper halide to yield a compound of formula (III) where $R^1$, $R^2$, $R^3$, $R^4$, $R^5$, X, W, n, and Ar are as defined in claim 5 and G represents $CH_2$—CH(J)—COOR group, where, R represents lower alkyl group and J represents a halogen atom.

7. A process for the preparation of a compound of formula (I)

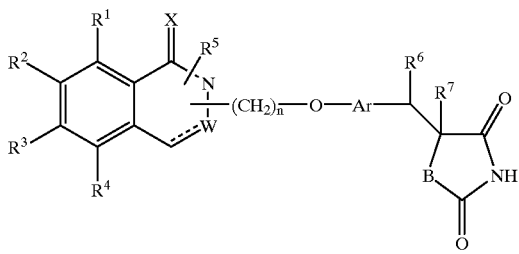

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro, or optionally substituted groups selected from alkyl, ($C_3$–$C_6$)cycloalkyl, alkoxy, cycloalkoxy, aryl, aralkyl, heteroaryl, heteroaralkyl, heterocyclyl wherein the heterocyclyl is selected from aziridinyl, pyrrolidinyl, morpholinyl, piperidinyl, or piperazinyl; aryloxy, alkoxycarbonyl, aralkoxycarbonyl, aryloxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino; carboxylic acid or its esters or amides; acyloxy, sulfonic acid or its esters or amides; "----" represents a bond; W represents a nitrogen atom; when $R^5$ is present on a carbon atom, it represents hydrogen, hydroxy, halogen, nitro, cyano or optionally substituted groups selected from amino, alkyl, ($C_3$–$C_6$)cycloalkyl, cycloalkoxy, acylamino, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its esters or amides, sulfonic acid and its esters or amides; when $R^5$ is present on a nitrogen atom, it represents hydrogen, or optionally substituted groups selected from alkyl, cycloalkyl, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, esters or amides of carboxylic acid, esters or amides of sulfonic acid; n is an integer ranging from 1–4; Ar represents optionally substituted groups selected from divalent phenylene, naphthlene, pyridyl, quinolinyl, benzofuryl, dihydrobenzofuryl, benzopyranyl, indolyl, indolinyl, azaindolyl, azaindolinyl, pyrazolyl, benzothiazolyl, and benzoxazolyl; $R^6$ and $R^7$ are the same or different and individually represent hydrogen atom, hydroxy, halogen or lower alkyl group or together form a bond; and B represents an oxygen atom or a sulfur atom; which comprises:

a) reacting the intermediate of formula (III)

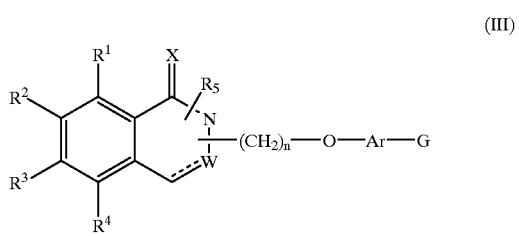

where G represents CHO group and all other groups are as defined above, with 2,4-thiazolidinedione or 2,4-oxazolidinedione and removing the water formed during the reaction to yield a compound of formula (X)

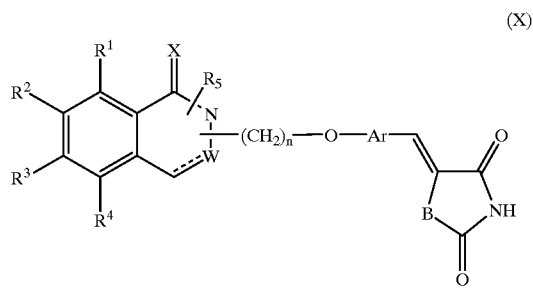

where $R^1$, $R^2$, $R^3$, $R^4$, $R^5$, X, W, n, Ar and B are as defined above;

b) reducing the compound of the formula (X) obtained in step (i) to obtain a compound of formula (XI)

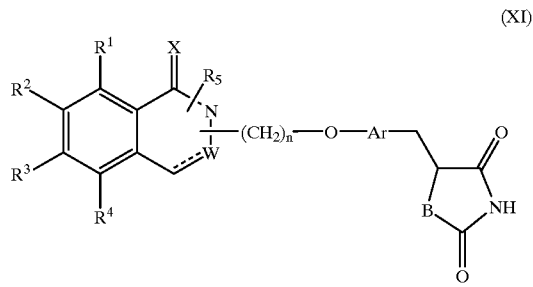

wherein $R^1$, $R^2$, $R^3$, $R^4$, $R^5$, X, W, n, Ar and B are as defined above, and optionally, c) converting the compounds of the formulas (X) and (XI) into their pharmaceutically acceptable salts, or their pharmaceutically acceptable solvates.

8. A compound of formula (I)

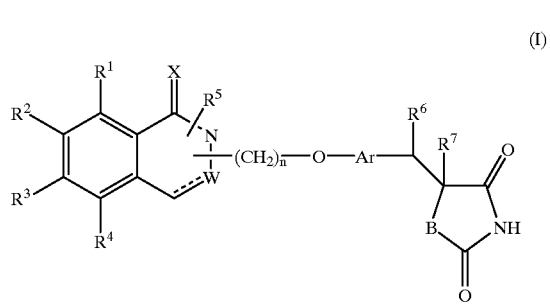

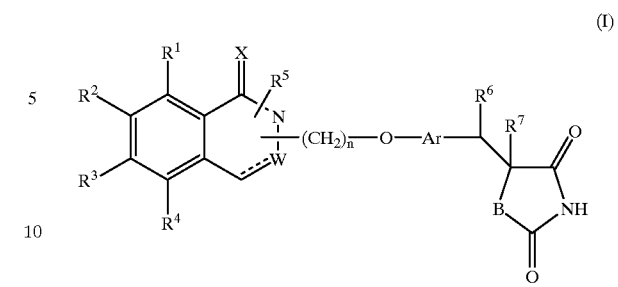

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro, or optionally substituted groups selected from alkyl, ($C_3$–$C_6$)cycloalkyl, alkoxy, cycloalkoxy, aryl, aralkyl, heteroaryl, heteroaralkyl, heterocyclyl wherein the heterocyclyl is selected from aziridinyl, pyrrolidinyl, morpholinyl, piperidinyl, or piperazinyl; aryloxy, alkoxycarbonyl, aralkoxycarbonyl, aryloxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its esters or amides, acyloxy, sulfonic acid or its esters or amides; "----" represents a bond; W represents a nitrogen atom; when $R^5$ is present on a carbon atom, it represents hydrogen, hydroxy, halogen, nitro, cyano or optionally substituted groups selected from amino, alkyl, ($C_3$–$C_6$)cycloalkyl, cycloalkoxy, acylamino, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its esters or amides, sulfonic acid and its esters or amides; when $R^5$ is present on a nitrogen atom, it represents hydrogen, or optionally substituted groups selected from alkyl, cycloalkyl, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, esters or amides of carboxylic acid, esters or amides of sulfonic acid; n is an integer ranging from 1–4; Ar represents optionally substituted groups selected from divalent phenylene, naphthlene, pyridyl, quinolinyl, benzofuryl, dihydrobenzofuryl, benzopyranyl, indolyl, indolinyl, azaindolyl, azaindolinyl, pyrazolyl, benzothiazolyl, and benzoxazolyl; $R^6$ and $R^7$ are the same or different and individually represent hydrogen atom, hydroxy, halogen or lower alkyl group or together form a bond; and B represents an oxygen atom or a sulfur atom prepared according to the process of claim 7.

9. A pharmaceutical composition which comprises a compound of formula (I) as defined in claim 1 as an active ingredient and a pharmaceutically acceptable carrier, diluent, excipient or solvate.

10. A pharmaceutical composition as claimed in claim 9, in the form of a tablet, capsule, powder, syrup, solution or suspension.

11. A method of preventing or treating diabetes caused by insulin resistance or complications of diabetes said diabetes caused by insulin resistance comprising administering a therapeutically effective amount of a compound of formula (I) as defined in claim 1, and a pharmaceutically acceptable carrier, diluent or excipient to a patient in need thereof.

12. A method according to claim 11 wherein the complication is dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephrithis, glomerular sclerosis, nephrotic syndrome, hypertensive nephrosclerosis, end-stage renal disease, microalbuminuria or eating disorders.

13. A method of reducing blood glucose, triglyceride or free fatty acids in a subject in need thereof comprising administering a therapeutically effective amount of a compound of formula (I), as defined in claim 1 and a pharmaceutically acceptable carrier, diluent or solvate.

14. A compound according to claim 1, which is selected from the group consisting of the compounds:
5-[4-[2-[4-Methyl-1-oxo-1,2-dihydrophthalazin-2-yl] ethoxy]phenyl methylene]thiazolidin-2,4-dione and its salts;
5-[4-[2-[1-Oxo-1,2-dihydrophthalazin-2-yl]ethoxy]phenyl methylene]thiazolidin-2,4-dione and its salts;
5-[4-[2-[4-Ethyl-1-oxo-1,2-dihydrophthalazin-2-yl]ethoxy] phenyl methylene]thiazolidin-2,4-dione and its salts;
5-[4-[2-[4-Phenyl-1-oxo-1,2-dihydrophthalazin-2-yl] ethoxy]phenyl methylene]thiazolidin-2,4-dione and its salts;
5-[4-[[2-Methyl-1-oxo-1,2-dihydrophthalazin-4-yl] methoxy]phenyl methylene]thiazolidin-2,4-dione and its salts;
5-[4-[2-[4-Methyl-1-oxo-1,2-dihydrophthalazin-2-yl] ethoxy]phenyl methyl] thiazolidin-2,4-dione and its salts;
5-[4-[2-[1-Oxo-1,2-dihydrophthalazin-2-yl]ethoxy]phenyl methyl]thiazolidin-2,4-dione and its salts
5-[4-[2-[4-Ethyl-1-oxo-1,2-dihydrophthalazin-2-yl]ethoxy] phenyl methyl]thiazolidin-2,4-dione and its salts;
5-[4-[2-[4-Phenyl-1-oxo-1,2-dihydrophthalazin-2-yl] ethoxy]phenyl methyl]thiazolidin-2,4-dione and its salts;
5-[4-[[2-Methyl-1-oxo-1,2-dihydrophthalazin-4-yl] methoxy]phenyl methyl]thiazolidin-2,4-dione and its salts;
5-[4-[2-[4-Hydroxy-1-oxo-1,2-dihydrophthalazin-2-yl] ethoxy]phenyl methylene]thiazolidin-2,4-dione and its salts; and
5-[4-[2-[4-Hydroxy-1-oxo-1,2-dihydrophthalazin-2-yl] ethoxy]phenyl methyl]thiazolidin-2,4-dione and its salts.

15. A pharmaceutical composition which comprises, a compound according to claim 14, as an active ingredient and a pharmaceutically acceptable carrier, diluent or excipient.

16. An intermediate of formula (III)

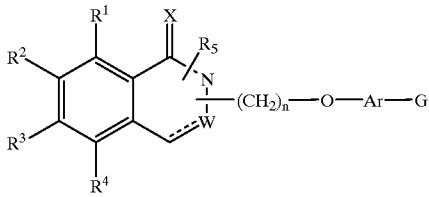

(III)

wherein X represents O or S; $R^1$, $R^2$, $R^3$, and $R^4$ are the same or different and represent hydrogen, halogen, hydroxy, cyano, nitro, or optionally substituted groups selected from alkyl, ($C_3$–$C_6$)cycloalkyl, alkoxy, cycloalkoxy, aryl, aralkyl, heteroaryl, heteroaralkyl, heterocyclyl wherein the heterocyclyl is selected from aziridinyl, pyrrolidinyl, morpholinyl, piperidinyl, or piperazinyl; aryloxy, alkoxycarbonyl, aryloxycarbonyl, aralkyoxycarbonyl, arylamino, amino, alkylamino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its esters or amides, acyloxy, sulfonic acid or its esters or amides; "----" represents a bond; W represents a nitrogen atom; when $R^5$ is present on a carbon atom, it represents hydrogen, hydroxy, halogen, nitro, cyano, or optionally substituted groups selected from amino, alkyl, ($C_3$–$C_6$)cycloalkyl, cycloalkoxy, acylamino, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, alkylamino, arylamino, alkoxycarbonylamino, aryloxycarbonylamino, aralkoxycarbonylamino, carboxylic acid and its esters or amides, sulfonic acid and its esters or amides; when $R^5$ is present on a nitrogen atom, it represents hydrogen or optionally substituted groups selected from alkyl, ($C_3$–$C_6$)cycloalkyl, aryl, aralkyl, heterocyclyl wherein the heterocyclyl is selected from aziridinyl, pyrrolidinyl, morpholinyl, piperidinyl, or piperazinyl; heteroaryl, heteroaralkyl, acyl, hydroxyalkyl, aminoalkyl, alkoxy, aryloxy, aralkoxy, acyloxy, alkoxycarbonyl, aryloxycarbonyl, aralkoxycarbonyl, alkoxyalkyl, alkylthio, thioalkyl, carboxylic acid or its esters or amides, or sulfonic acid or its esters or amides; n is an integer ranging from 1–4; Ar represents optionally substituted groups selected from divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl, and benzoxazolyl; G represents CHO, $NO_2$, —$NH_2$ or —$CH_2CH(J)COOR$, where J represents a halogen atom and R represents H or lower alkyl group prepared by the process comprising the steps of:

a) reacting a compound of formula (IV)

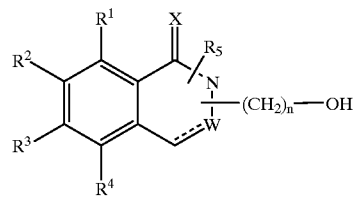

(IV)

wherein, $R^1$, $R^2$, $R^3$, $R^4$, $R^5$, X, W, and n are as defined above with a compound of formula (V)

$L^1$—Ar—G  (V)

where $L^1$ is a halogen atom, G is a CHO or a $NO_2$ group and Ar is as defined above;

b) reacting a compound of formula (VI)

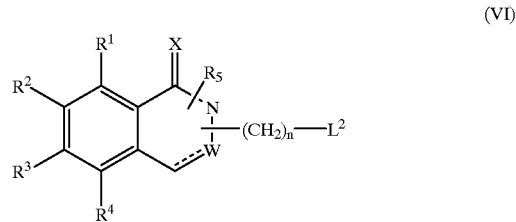

(VI)

where $R^1$, $R^2$, $R^3$, $R^4$, $R^5$, X, W, and n are as defined above and $L^2$ is a halogen atom or a leaving group with a compound of formula (VII)

HO—Ar—G  (VII)

where G is a CHO or $NO_2$ group and Ar is as defined above;

c) reacting a compound of formula (IV)

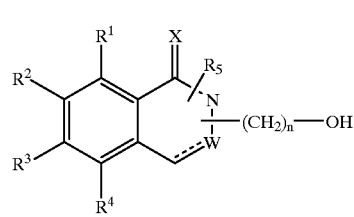

(IV)

wherein, $R^1$, $R^2$, $R^3$, $R^4$, $R^5$, X, W, and n are as defined above, with a compound of formula (VII)

HO—Ar—G  (VII)

where G is a CHO or $NO_2$ group and Ar is as defined above;

d) reacting a compound of formula (VIII)

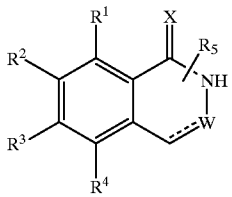
(VIII)

where $R^1$, $R^2$, $R^3$, $R^4$, $R^5$, X and W are as defined above, with a compound of formula (IX)

$L^2$—$(CH_2)_n$—Ar—G  (IX)

where n, Ar and G are as defined above and $L^2$ is a leaving group; and e) diazotizating a compound of formula (XIV)

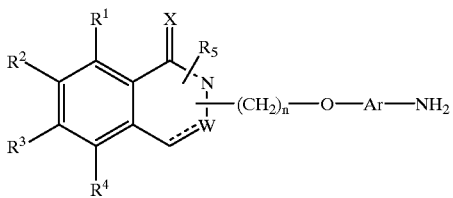
(XIV)

wherein, $R^1$, $R^2$, $R^3$, $R^4$, $R^5$, X, W, n, and Ar are as defined above, followed by treatment with acrylic acid ester in the presence of hydrohalo acids and copper oxide or copper halide to yield a compound of formula (III) where $R^1$, $R^2$, $R^3$, $R^4$, $R^5$, X, W, n, and Ar are as defined above and G represents $CH_2$—CH(J)—COOR group, where, R represents lower alkyl group and J represents a halogen atom.

17. A method of preventing or treating diabetes caused by insulin resistance or complications of diabetes said diabetes caused by insulin resistance comprising administering a therapeutically effective amount of a compound of formula (I) as defined in claim 14, and a pharmaceutically acceptable carrier, diluent or excipient to a patient in need thereof.

18. A method according to claim 17 wherein the complication is dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephrithis, glomerular sclerosis, nephrotic syndrome, hypertensive nephrosclerosis, end-stage renal disease, microalbuminuria or eating disorders.

19. A method of reducing blood glucose, triglyceride or free fatty acids in a subject in need thereof comprising administering a therapeutically effective amount of a compound of formula (I), as defined in claim 14 and a pharmaceutically acceptable carrier, diluent or solvate.

* * * * *